US005847083A

United States Patent [19]
Halazonetis

[11] Patent Number: 5,847,083
[45] Date of Patent: Dec. 8, 1998

[54] MODIFIED P53 CONSTRUCTS WHICH ENHANCE DNA BINDING

[75] Inventor: Thanos D. Halazonetis, Philadelphia, Pa.

[73] Assignee: The Wistar Institute of Anatomy and Biology, Philadelphia, Pa.

[21] Appl. No.: 697,221

[22] Filed: Aug. 21, 1996

[51] Int. Cl.$^6$ .................... C07K 14/435; C07K 14/47; C12N 15/12; C12N 15/63
[52] U.S. Cl. .................... 530/358; 435/69.1; 435/320.1; 536/23.4; 536/23.5
[58] Field of Search ............................... 435/69.1, 69.7, 435/172.1, 320.1; 514/2; 530/358; 536/23.4, 23.5

[56] References Cited

U.S. PATENT DOCUMENTS

| | | | |
|---|---|---|---|
| 5,362,623 | 11/1994 | Vogelstein et al. | 435/6 |
| 5,569,824 | 10/1996 | Donehower et al. | 800/2 |
| 5,573,925 | 11/1996 | Halazonetis | 435/69.7 |

FOREIGN PATENT DOCUMENTS

| | | |
|---|---|---|
| 390323 | 10/1990 | European Pat. Off. . |
| 475623 | 3/1992 | European Pat. Off. . |
| 518650 | 12/1992 | European Pat. Off. . |
| WO93/22430 | 11/1993 | WIPO . |
| WO94/06910 | 3/1994 | WIPO . |
| WO94/10306 | 5/1994 | WIPO . |
| WO94/12202 | 6/1994 | WIPO . |
| WO94/16716 | 8/1994 | WIPO . |
| WO95/17213 | 6/1995 | WIPO . |
| WO96/16989 | 6/1996 | WIPO . |

OTHER PUBLICATIONS

Brugidou et al. The retro–inverso form of a homeobox-–derived short peptide is rapidly internalized by cultured neurons: a new basis for an efficient intracelular delivery system. Biochemical and Biophysical Research Communications. vol. 214, No. 2, pp. 685–693, Sep. 14, 1995.
Mayr et al. Sequence of an exon of the canine p53 gene—mutation in a papilloma. British Verterinary Journal. vol. 150, pp. 81–84, 1994.
T. Halazonetis et al, "Conformational Shifts Propagate from the Oligomerization Domain of p53 to its Tetrameric DNA Binding Domain and Restore DNA Binding to Select p53 Mutants", *EMBO J.*, 12(13):5057–5064 (Dec., 1993) [Halazonetis I].
T. Halazonetis et al, "Wild–Type p53 Adopts a 'Mutant-'–Like Conformation when Bound to DNA", *EMBO J.*, 12(3):1021–1028 (Mar., 1993) [Halazonetis II].
Y. Wang et al, "p53 Domains: Identification and Characterization of Two Autonomous DNA–Binding Regions", *Genes & Development*, 7:2575–2586 (Dec., 1993) [Wang I].
P. Wang et al, "p53 Domains: Structure, Oligomerization, and Transformation", *Mol. Cell. Biol.*, 14(8):5182–5191 (Aug., 1994) [Wang II].
T. Hupp et al, "Regulation of the Specific DNA Binding Function of p53", *Cell*, 71:875–886 (Nov. 27, 1992) [Hupp I].

T. Hupp et al, "Activation of the Cryptic DNA Binding Function of Mutant Forms of p53", *Nucl. Acids Res.*, 21(14):3167–3174 (Jul. 14, 1993) [Hupp II].
T. Fujiwara et al, "A Retroviral Wild–type p53 Expression Vector Penetrates Human Lung Cancer Spheroids and Inhibits Growth by Inducing Apoptosis", *Cancer Res.*, 53:4129–4133 (Sep. 15, 1993) [Fujiwara I].
T. Fujiwara et al, "Induction of Chemosensitivity in Human Lung Cancer Cells in vivo by Adenovirus–Mediated Transfer of the Wild–Type p53 Gene", *Cancer Res.*, 54:2287–2291 (May 1, 1994) [Fujiwara II].
G. Shaulsky et al, "Nuclear Localization is Essential for the Activity of p53 Protein", *Oncogene*, 6:2056–2065 (Nov., 1991) [Shaulsky I].
G. Shaulsky et al, "Nuclear Accumulation of p53 Protein is Mediated by Several Nuclear Localization Signals and Plays a Role in Tumorigenesis", *Mol. Cell. Biol.*, 10(12):6565–6577 (Dec., 1990) [Shaulsky II].
J. Oliner et al, "Amplification of a Gene Encoding a p53–Associated Protein in Human Sarcomas", *Nature*, 358:80–83 (Jul. 2, 1992) [Oliner I].
J. Oliner et al, "Oncoprotein MDM2 Conceals the Activation Domain of Tumour Suppressor p53", *Nature*, 362:857–860 (Apr. 29, 1993) [Oliner II].
J. Chen et al, "Heterogeneity of Transcriptional Activity of Mutant p53 Proteins and p53 DNA Target Sequences", *Oncogene*, 8:2159–2166 (Aug. 1993) [Chen I].
J. Chen et al, "Mapping of the p53 and mdm–2 Interaction Domains", *Mol. Cell. Biol.*, 13(7):4107–4114 (Jul., 1993) [Chen II].
C. Harris, "p53: At the Crossroads of Molecular Carcinogenesis and Risk Assessment", *Science*, 262:1980–1981 (Dec. 24, 1993).
R. Zakut–Houri et al, "Human p53 Cellular Tumor Antigen: cDNA Sequence and Expression in COS Cells", *EMBO J.*, 4(5):1251–1255 (May, 1985).
T. Soussi et al, "Structural Aspects of the p53 Protein in Relation to Gene Evolution", *Oncogene*, 5:945–952 (Jul., 1990).
J. Pietenpol et al, "Sequence–Specific Transcriptional Activation is Essential for Growth Suppression by p53", *Proc. Natl. Acad. Sci. USA*, 91:1998–2002 (Mar., 1994).
S. Kraiss et al, "Oligomerization of Oncoprotein p53", *J. Virol.*, 62(12):4737–4744 (Dec., 1988).
T. Friedmann, "Gene Therapy of Cancer Through Restoration of Tumor–Suppressor Functions", *Cancer Supplement*, 70(6):1810–1817 (Sep. 15, 1992).
P. Friedman et al, "The p53 Protein is an Unusually Shaped Tetramer that Binds Directly to DNA", *Proc. Natl. Acad. Sci. USA*, 90:3319–3323 (Apr., 1993).

(List continued on next page.)

Primary Examiner—Stephen Walsh
Assistant Examiner—Michael Pak
Attorney, Agent, or Firm—Howson and Howson

[57] ABSTRACT

A modified p53 protein or peptide having DNA binding in which amino acid residue 284 of a p53 protein or protein fragment is changed to Arginine or Lysine, is described. Also described are nucleotide sequences encoding the modified protein and vectors capable of expressing it.

18 Claims, 3 Drawing Sheets

OTHER PUBLICATIONS

P. Hainaut et al, "Analysis of p53 Quaternary Structure in Relation to Sequence–Specific DNA Binding", *Oncogene,* 9:299–303 (Jan., 1994).

W. El–Deiry et al, "WAF1, a Potential Mediator of p53 Tumor Suppression", *Cell,* 75:817–825 (Nov. 19, 1993).

X. Wu et al, "The p53–mdm–2 Autoregulatory Feedback Loop", *Genes & Development,* 7:1126–1132 (Jul., 1993).

M. Kastan et al, "A Mammalian Cell Cycle Checkpoint Pathway Utilizing p53 and GADD45 is Defective in Ataxia–Telangiectasia", *Cell,* 71:587–597 (Nov. 13, 1992).

N. Pavletich et al, "The DNA–Binding Domain of p53 Contains the Four Conserved Regions and the Major Mutation Hot Spots", *Genes & Development,* 7:2556–2564 (Dec., 1993).

S. Fields et al, "Presence of a Potent Transcription Activating Sequence in the p53 Protein", *Science,* 249:1046–1049 (Aug. 31, 1990).

J. Bargonetti et al, "Site–Specific Binding of Wild–Type p53 to Cellular DNA is Inhibited by SV40 T Antigen and Mutant p53", *Genes & Development,* 6:1886–1898 (Oct., 1992).

C. Finlay et al, "The p53 Proto–Oncogene can Act as a Suppressor of Transformation", *Cell,* 57:1083–1093 (Jun. 30, 1989).

D. Eliyahu et al, "Wild–Type p53 can Inhibit Oncogene–Mediated Focus Formation", *Proc. Natl. Acad. Sci. USA,* 86:8763–8767 (Nov., 1989).

S. Baker et al, "Suppression of Human Colorectal Carcinoma Cell Growth by Wild–Type p53", *Science,* 249:912–915 (Aug. 24, 1990).

W. Mercer et al, "Negative Growth Regulation in a Glioblastoma Tumor Cell Line that Conditionally Expresses Human Wild–Type p53", *Proc. Natl. Acad. Sci. USA,* 87:6166–6170 (Aug., 1990).

W. Isaacs et al, "Wild–Type p53 Suppresses Growth of Human Prostate Cancer Cells Containing Mutant p53 Alleles", *Cancer Res.,* 51:4716–4720 (Sep. 1, 1991).

S. Kern et al, "Oncogenic Forms of p53 Inhibit p53–Regulated Gene Expression", *Science,* 256:827–830 (May 8, 1992).

E. Yonish–Rouach et al, "p53–Mediated Cell Death: Relationship to Cell Cycle Control", *Mol. Cell. Biol.,* 13(3):1415–1423 (Mar., 1993).

S. Lowe et al, "p53–Dependent Apoptosis Modulates the Cytotoxicity of Anticancer Agents", *Cell,* 74:957–967 (Sep. 24, 1993).

J. Milner et al, "Cotranslation of Activated Mutant p53 with Wild Type Drives the Wild–Type p53 Protein into the Mutant Conformation", *Cell,* 65:765–774 (May 31, 1991).

G. Farmer et al, "Wild–Type p53 Activates Transcription in vitro", *Nature,* 358:83–86 (Jul. 2, 1992).

H. Sakamoto et al, "Specific Sequences from the Carboxyl Terminus of Human p53 Gene Product Form Anti–Parallel Tetramers in Solution", *Proc. Natl. Acad. Sci. USA,* 91:8974–8978 (Sep., 1994).

J. Momand et al, "The mdm–2 Oncogene Product Forms a Complex with the p53 Protein and Inhibits p53–Mediated Transactivation", *Cell,* 69:1237–1245 (Jun. 26, 1992).

J. Lin et al, "Several Hydrophobic Amino Acids in the p53 Amino–Terminal Domain are Required for Transcriptional Activation, Binding to mdm–2 and the Adenovirus 5 E1B 55–KD Protein", *Genes & Development,* 8:1235–1246 (May, 1994).

L. Cox et al, "Xenopus p53 is Biochemically Similar to the Human Tumour Suppressor Protein p53 and is Induced upon DNA Damage in Somatic Cells", *Oncogene,* 9:2951–2959 (Oct., 1994).

B. Li et al, "Preferential Overexpression of a 172Arg–Leu Mutant p53 in the Mammary Gland of Transgenic Mice Results in Altered Lobuloalveolar Development", *Cell Growth and Differentiation,* 5:711–721 (Jul., 1994).

J. Richardson et al, "Amino Acid Preferences for Specific Locations at the Ends of alpha Helices", *Science,* 240:1648–1652 (Jun. 17, 1988).

A. Chumakov et al, "Analysis of p53 Transactivation through High–Affinity Binding Sites", *Oncogene,* 8:3005–3011 (Nov., 1993).

C. Caron de Fromentel et al, "TP53 Tumor Suppressor Gene: A Model for Investigating Human Mutagenesis", *Genes, Chrom. and Cancer,* 4:1–15 (Jan., 1992).

E. Shaulian et al, "Tight DNA Binding and Oligomerization are Dispensable for the Ability of p53 to Transactivate Target Genes and Suppress Transformation", *EMBO J.,* 12(7):2789–2797 (Jul., 1993).

S. Maheswaran et al, "Physical and Functional Interaction Between WT1 and p53 Proteins", *Proc. Natl. Acad. Sci. USA,* 90:5100–5104 (Jun., 1993).

T. Unger et al, "p53: a Transdominant Regulator of Transcription whose Function is Ablated by Mutations Occurring in Human Cancer", *EMBO J.,* 11(4):1383–1390 (Apr., 1992) [Unger I].

T. Unger et al, "Functional Domains of Wild–Type and Mutant p53 Proteins Involved in Transcriptional Regulation, Transdominant Inhibition, and Transformation Suppression", *Mol. Cell. Biol.,* 13(9):5186–5194 (Sep., 1993) [Unger II].

M. Reed et al, "p53 Domains: Suppression, Transformation, and Transactivation", *Gene Expression,* 3(1):95–107 (May, 1993).

C. Miller et al, "Mutant p53 Proteins Having Diverse Intracellular Abilities to Oligomerize and Activate Transcription", *Oncogene,* 8(7):1815–1824 (Jun., 1993).

K. Iwabuchi et al, "Use of the Two–Hybrid System to Identify the Domain of p53 Involved in Oligomerization", *Oncogene,* 8(6):1693–1696 (May, 1993).

T. Fujiwara et al, "Gene Therapeutics and Gene Therapy for Cancer", *Curr. Opin. Oncol.,* 6:96–105 (Jan., 1994) [Fujiwara III].

H–W. Sturzbecher et al, "A C–Terminal a–helix Plus Basic Region Motif is the Major Structural Determinant of p53 Tetramerization", *Oncogene,* 7:1513–1523 (Jun., 1992).

T. Hupp et al, "Allosteric Activation of Latent p53 Tetramers", *Current Biology,* 4(10):865–875 (Oct., 1994) [Hupp III].

Y. Cho et al, "Crystal Structure of a p53 Tumor Suppressor–DNA Complex: Understanding Tumorigenic Mutations", *Science,* 265:346–355 (Jul., 1994).

C. Finlay et al, "Activating Mutations for Transformation by p53 Produce a Gene Product that Forms an hsc70–p53 Complex with an Altered Half–Life", *Mol. Cell. Biol.,* 8(2):531–539 (Feb., 1988).

M. Hollstein et al, "p53 Mutations in Human Cancers", *Science,* 253:49–53 (Jul., 1991).

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
        ( A ) LENGTH: 1317 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 136..1314

( x i ) SEQUENCE DESCRIPTION: SEQ ID NO:1:

```
GTCTAGAGCC  ACCGTCCAGG  GAGCAGGTAG  CTGCTGGGCT  CCGGGGACAC  TTTGCGTTCG     60

GGCTGGGAGC  GTGCTTTCCA  CGACGGTGAC  ACGCTTCCCT  GGATTGGCAG  CCAGACTGCC    120
```

| | | | | | | | | | | | | | | | | |
|---|---|---|---|---|---|---|---|---|---|---|---|---|---|---|---|---|
| TTCCGGGTCA | CTGCC | ATG | GAG | GAG | CCG | CAG | TCA | GAT | CCT | AGC | GTC | GAG | CCC | | | 171 |
| | | Met | Glu | Glu | Pro | Gln | Ser | Asp | Pro | Ser | Val | Glu | Pro | | | |
| | | 1 | | | 5 | | | | | | 10 | | | | | |
| CCT | CTG | AGT | CAG | GAA | ACA | TTT | TCA | GAC | CTA | TGG | AAA | CTA | CTT | CCT | GAA | 219 |
| Pro | Leu | Ser | Gln | Glu | Thr | Phe | Ser | Asp | Leu | Trp | Lys | Leu | Leu | Pro | Glu | |
| | | 15 | | | | | 20 | | | | | 25 | | | | |
| AAC | AAC | GTT | CTG | TCC | CCC | TTG | CCG | TCC | CAA | GCA | ATG | GAT | GAT | TTG | ATG | 267 |
| Asn | Asn | Val | Leu | Ser | Pro | Leu | Pro | Ser | Gln | Ala | Met | Asp | Asp | Leu | Met | |
| | | 30 | | | | | 35 | | | | | 40 | | | | |
| CTG | TCC | CCG | GAC | GAT | ATT | GAA | CAA | TGG | TTC | ACT | GAA | GAC | CCA | GGT | CCA | 315 |
| Leu | Ser | Pro | Asp | Asp | Ile | Glu | Gln | Trp | Phe | Thr | Glu | Asp | Pro | Gly | Pro | |
| 45 | | | | | 50 | | | | | 55 | | | | | 60 | |
| GAT | GAA | GCT | CCC | AGA | ATG | CCA | GAG | GCT | GCT | CCC | CCC | GTG | GCC | CCT | GCA | 363 |
| Asp | Glu | Ala | Pro | Arg | Met | Pro | Glu | Ala | Ala | Pro | Pro | Val | Ala | Pro | Ala | |
| | | | | 65 | | | | | 70 | | | | | 75 | | |
| CCA | GCA | GCT | CCT | ACA | CCG | GCG | GCC | CCT | GCA | CCA | GCC | CCC | TCC | TGG | CCC | 411 |
| Pro | Ala | Ala | Pro | Thr | Pro | Ala | Ala | Pro | Ala | Pro | Ala | Pro | Ser | Trp | Pro | |
| | | 80 | | | | | 85 | | | | | 90 | | | | |
| CTG | TCA | TCT | TCT | GTC | CCT | TCC | CAG | AAA | ACC | TAC | CAG | GGC | AGC | TAC | GGT | 459 |
| Leu | Ser | Ser | Ser | Val | Pro | Ser | Gln | Lys | Thr | Tyr | Gln | Gly | Ser | Tyr | Gly | |
| | | 95 | | | | | 100 | | | | | 105 | | | | |
| TTC | CGT | CTG | GGC | TTC | TTG | CAT | TCT | GGG | ACA | GCC | AAG | TCT | GTA | ACT | TGC | 507 |
| Phe | Arg | Leu | Gly | Phe | Leu | His | Ser | Gly | Thr | Ala | Lys | Ser | Val | Thr | Cys | |
| 110 | | | | | 115 | | | | | 120 | | | | | | |
| ACG | TAC | TCC | CCT | GCC | CTC | AAC | AAG | ATG | TTT | TGC | CAA | CTG | GCC | AAG | ACC | 555 |
| Thr | Tyr | Ser | Pro | Ala | Leu | Asn | Lys | Met | Phe | Cys | Gln | Leu | Ala | Lys | Thr | |
| 125 | | | | | 130 | | | | | 135 | | | | | 140 | |
| TGC | CCT | GTG | CAG | CTG | TGG | GTT | GAT | TCC | ACA | CCC | CCG | CCC | GGC | ACC | CGC | 603 |
| Cys | Pro | Val | Gln | Leu | Trp | Val | Asp | Ser | Thr | Pro | Pro | Pro | Gly | Thr | Arg | |
| | | | | 145 | | | | | 150 | | | | | 155 | | |
| GTC | CGC | GCC | ATG | GCC | ATC | TAC | AAG | CAG | TCA | CAG | CAC | ATG | ACG | GAG | GTT | 651 |
| Val | Arg | Ala | Met | Ala | Ile | Tyr | Lys | Gln | Ser | Gln | His | Met | Thr | Glu | Val | |
| | | | 160 | | | | | 165 | | | | | 170 | | | |
| GTG | AGG | CGC | TGC | CCC | CAC | CAT | GAG | CGC | TGC | TCA | GAT | AGC | GAT | GGT | CTG | 699 |
| Val | Arg | Arg | Cys | Pro | His | His | Glu | Arg | Cys | Ser | Asp | Ser | Asp | Gly | Leu | |
| | | 175 | | | | | 180 | | | | | 185 | | | | |
| GCC | CCT | CCT | CAG | CAT | CTT | ATC | CGA | GTG | GAA | GGA | AAT | TTG | CGT | GTG | GAG | 747 |
| Ala | Pro | Pro | Gln | His | Leu | Ile | Arg | Val | Glu | Gly | Asn | Leu | Arg | Val | Glu | |
| | | 190 | | | | | 195 | | | | | 200 | | | | |
| TAT | TTG | GAT | GAC | AGA | AAC | ACT | TTT | CGA | CAT | AGT | GTG | GTG | GTG | CCC | TAT | 795 |
| Tyr | Leu | Asp | Asp | Arg | Asn | Thr | Phe | Arg | His | Ser | Val | Val | Val | Pro | Tyr | |
| 205 | | | | | 210 | | | | | 215 | | | | | 220 | |
| GAG | CCG | CCT | GAG | GTT | GGC | TCT | GAC | TGT | ACC | ACC | ATC | CAC | TAC | AAC | TAC | 843 |
| Glu | Pro | Pro | Glu | Val | Gly | Ser | Asp | Cys | Thr | Thr | Ile | His | Tyr | Asn | Tyr | |
| | | | | 225 | | | | | 230 | | | | | 235 | | |
| ATG | TGT | AAC | AGT | TCC | TGC | ATG | GGC | GGC | ATG | AAC | CGG | AGA | CCC | ATC | CTC | 891 |
| Met | Cys | Asn | Ser | Ser | Cys | Met | Gly | Gly | Met | Asn | Arg | Arg | Pro | Ile | Leu | |
| | | | 240 | | | | | 245 | | | | | 250 | | | |
| ACC | ATC | ATC | ACA | CTG | GAA | GAC | TCC | AGT | GGT | AAT | CTA | CTG | GGA | CGG | AAC | 939 |
| Thr | Ile | Ile | Thr | Leu | Glu | Asp | Ser | Ser | Gly | Asn | Leu | Leu | Gly | Arg | Asn | |
| | | 255 | | | | | 260 | | | | | 265 | | | | |
| AGC | TTT | GAG | GTG | CGT | GTT | TGT | GCC | TGT | CCT | GGG | AGA | GAC | CGG | CGC | ACA | 987 |
| Ser | Phe | Glu | Val | Arg | Val | Cys | Ala | Cys | Pro | Gly | Arg | Asp | Arg | Arg | Thr | |
| | | 270 | | | | | 275 | | | | | 280 | | | | |
| GAG | GAA | GAG | AAT | CTC | CGC | AAG | AAA | GGG | GAG | CCT | CAC | CAC | GAG | CTG | CCC | 1035 |
| Glu | Glu | Glu | Asn | Leu | Arg | Lys | Lys | Gly | Glu | Pro | His | His | Glu | Leu | Pro | |
| 285 | | | | | 290 | | | | | 295 | | | | | 300 | |
| CCA | GGG | AGC | ACT | AAG | CGA | GCA | CTG | CCC | AAC | AAC | ACC | AGC | TCC | TCT | CCC | 1083 |
| Pro | Gly | Ser | Thr | Lys | Arg | Ala | Leu | Pro | Asn | Asn | Thr | Ser | Ser | Ser | Pro | |
| | | | | 305 | | | | | 310 | | | | | 315 | | |

| | | | | | | | | | | | | | | | |
|---|---|---|---|---|---|---|---|---|---|---|---|---|---|---|---|
| CAG | CCA | AAG | AAG | AAA | CCA | CTG | GAT | GGA | GAA | TAT | TTC | ACC | CTT | CAG | ATC |
| Gln | Pro | Lys | Lys | Lys | Pro | Leu | Asp | Gly | Glu | Tyr | Phe | Thr | Leu | Gln | Ile |
| | | 320 | | | | | | 325 | | | | | 330 | | |

1131

| CGT | GGG | CGT | GAG | CGC | TTC | GAG | ATG | TTC | CGA | GAG | CTG | AAT | GAG | GCC | TTG |
|---|---|---|---|---|---|---|---|---|---|---|---|---|---|---|---|
| Arg | Gly | Arg | Glu | Arg | Phe | Glu | Met | Phe | Arg | Glu | Leu | Asn | Glu | Ala | Leu |
| | | 335 | | | | | 340 | | | | | 345 | | | |

1179

| GAA | CTC | AAG | GAT | GCC | CAG | GCT | GGG | AAG | GAG | CCA | GGG | GGG | AGC | AGG | GCT |
|---|---|---|---|---|---|---|---|---|---|---|---|---|---|---|---|
| Glu | Leu | Lys | Asp | Ala | Gln | Ala | Gly | Lys | Glu | Pro | Gly | Gly | Ser | Arg | Ala |
| 350 | | | | | 355 | | | | | 360 | | | | | |

1227

| CAC | TCC | AGC | CAC | CTG | AAG | TCC | AAA | AAG | GGT | CAG | TCT | ACC | TCC | CGC | CAT |
|---|---|---|---|---|---|---|---|---|---|---|---|---|---|---|---|
| His | Ser | Ser | His | Leu | Lys | Ser | Lys | Lys | Gly | Gln | Ser | Thr | Ser | Arg | His |
| 365 | | | | | 370 | | | | | 375 | | | | | 380 |

1275

| AAA | AAA | CTC | ATG | TTC | AAG | ACA | GAA | GGG | CCT | GAC | TCA | GAC | TGA | | |
|---|---|---|---|---|---|---|---|---|---|---|---|---|---|---|---|
| Lys | Lys | Leu | Met | Phe | Lys | Thr | Glu | Gly | Pro | Asp | Ser | Asp | | | |
| | | | | 385 | | | | | 390 | | | | | | |

1317

( 2 ) INFORMATION FOR SEQ ID NO:2:

( i ) SEQUENCE CHARACTERISTICS:
        ( A ) LENGTH: 393 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Glu | Glu | Pro | Gln | Ser | Asp | Pro | Ser | Val | Glu | Pro | Pro | Leu | Ser | Gln |
|---|---|---|---|---|---|---|---|---|---|---|---|---|---|---|---|
| 1 | | | | 5 | | | | | 10 | | | | | 15 | |

| Glu | Thr | Phe | Ser | Asp | Leu | Trp | Lys | Leu | Leu | Pro | Glu | Asn | Asn | Val | Leu |
|---|---|---|---|---|---|---|---|---|---|---|---|---|---|---|---|
| | | | 20 | | | | | 25 | | | | | 30 | | |

| Ser | Pro | Leu | Pro | Ser | Gln | Ala | Met | Asp | Asp | Leu | Met | Leu | Ser | Pro | Asp |
|---|---|---|---|---|---|---|---|---|---|---|---|---|---|---|---|
| | | | 35 | | | | | 40 | | | | | 45 | | |

| Asp | Ile | Glu | Gln | Trp | Phe | Thr | Glu | Asp | Pro | Gly | Pro | Asp | Glu | Ala | Pro |
|---|---|---|---|---|---|---|---|---|---|---|---|---|---|---|---|
| | 50 | | | | | 55 | | | | | 60 | | | | |

| Arg | Met | Pro | Glu | Ala | Ala | Pro | Pro | Val | Ala | Pro | Ala | Pro | Ala | Ala | Pro |
|---|---|---|---|---|---|---|---|---|---|---|---|---|---|---|---|
| 65 | | | | | 70 | | | | | 75 | | | | | 80 |

| Thr | Pro | Ala | Ala | Pro | Ala | Pro | Ala | Pro | Ser | Trp | Pro | Leu | Ser | Ser | Ser |
|---|---|---|---|---|---|---|---|---|---|---|---|---|---|---|---|
| | | | | 85 | | | | | 90 | | | | | 95 | |

| Val | Pro | Ser | Gln | Lys | Thr | Tyr | Gln | Gly | Ser | Tyr | Gly | Phe | Arg | Leu | Gly |
|---|---|---|---|---|---|---|---|---|---|---|---|---|---|---|---|
| | | | | 100 | | | | | 105 | | | | | 110 | |

| Phe | Leu | His | Ser | Gly | Thr | Ala | Lys | Ser | Val | Thr | Cys | Thr | Tyr | Ser | Pro |
|---|---|---|---|---|---|---|---|---|---|---|---|---|---|---|---|
| | | | 115 | | | | | 120 | | | | | 125 | | |

| Ala | Leu | Asn | Lys | Met | Phe | Cys | Gln | Leu | Ala | Lys | Thr | Cys | Pro | Val | Gln |
|---|---|---|---|---|---|---|---|---|---|---|---|---|---|---|---|
| | | | 130 | | | | | 135 | | | | | 140 | | |

| Leu | Trp | Val | Asp | Ser | Thr | Pro | Pro | Pro | Gly | Thr | Arg | Val | Arg | Ala | Met |
|---|---|---|---|---|---|---|---|---|---|---|---|---|---|---|---|
| 145 | | | | | 150 | | | | | 155 | | | | | 160 |

| Ala | Ile | Tyr | Lys | Gln | Ser | Gln | His | Met | Thr | Glu | Val | Val | Arg | Arg | Cys |
|---|---|---|---|---|---|---|---|---|---|---|---|---|---|---|---|
| | | | | 165 | | | | | 170 | | | | | 175 | |

| Pro | His | His | Glu | Arg | Cys | Ser | Asp | Ser | Asp | Gly | Leu | Ala | Pro | Pro | Gln |
|---|---|---|---|---|---|---|---|---|---|---|---|---|---|---|---|
| | | | | 180 | | | | | 185 | | | | | 190 | |

| His | Leu | Ile | Arg | Val | Glu | Gly | Asn | Leu | Arg | Val | Glu | Tyr | Leu | Asp | Asp |
|---|---|---|---|---|---|---|---|---|---|---|---|---|---|---|---|
| | | | 195 | | | | | 200 | | | | | 205 | | |

| Arg | Asn | Thr | Phe | Arg | His | Ser | Val | Val | Val | Pro | Tyr | Glu | Pro | Pro | Glu |
|---|---|---|---|---|---|---|---|---|---|---|---|---|---|---|---|
| | | 210 | | | | | 215 | | | | | 220 | | | |

| Val | Gly | Ser | Asp | Cys | Thr | Thr | Ile | His | Tyr | Asn | Tyr | Met | Cys | Asn | Ser |
|---|---|---|---|---|---|---|---|---|---|---|---|---|---|---|---|
| 225 | | | | | 230 | | | | | 235 | | | | | 240 |

| Ser | Cys | Met | Gly | Gly | Met | Asn | Arg | Arg | Pro | Ile | Leu | Thr | Ile | Ile | Thr |
|---|---|---|---|---|---|---|---|---|---|---|---|---|---|---|---|
| | | | | 245 | | | | | 250 | | | | | 255 | |

```
Leu  Glu  Asp  Ser  Ser  Gly  Asn  Leu  Leu  Gly  Arg  Asn  Ser  Phe  Glu  Val
               260                 265                      270

Arg  Val  Cys  Ala  Cys  Pro  Gly  Arg  Asp  Arg  Arg  Thr  Glu  Glu  Glu  Asn
               275                 280                      285

Leu  Arg  Lys  Lys  Gly  Glu  Pro  His  His  Glu  Leu  Pro  Pro  Gly  Ser  Thr
     290                      295                      300

Lys  Arg  Ala  Leu  Pro  Asn  Asn  Thr  Ser  Ser  Ser  Pro  Gln  Pro  Lys  Lys
305                           310                 315                      320

Lys  Pro  Leu  Asp  Gly  Glu  Tyr  Phe  Thr  Leu  Gln  Ile  Arg  Gly  Arg  Glu
                    325                      330                      335

Arg  Phe  Glu  Met  Phe  Arg  Glu  Leu  Asn  Glu  Ala  Leu  Glu  Leu  Lys  Asp
               340                 345                      350

Ala  Gln  Ala  Gly  Lys  Glu  Pro  Gly  Gly  Ser  Arg  Ala  His  Ser  Ser  His
               355                 360                      365

Leu  Lys  Ser  Lys  Lys  Gly  Gln  Ser  Thr  Ser  Arg  His  Lys  Lys  Leu  Met
     370                      375                      380

Phe  Lys  Thr  Glu  Gly  Pro  Asp  Ser  Asp
385                      390
```

( 2 ) INFORMATION FOR SEQ ID NO:3:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:3:

```
Met  Glu  Glu  Pro  Gln  Ser  Asp  Pro  Ser  Val  Glu  Pro  Pro  Leu  Ser  Gln
1                   5                   10                      15

Glu  Thr  Phe  Ser  Asp  Leu  Trp  Lys  Leu  Leu  Pro  Glu  Asn  Asn  Val  Leu
               20                  25                      30

Ser  Pro  Leu  Pro  Ser  Gln  Ala  Met  Asp  Asp  Leu  Met  Leu  Ser  Pro  Asp
               35                  40                      45

Asp  Ile  Glu  Gln  Trp  Phe  Thr  Glu  Asp  Pro  Gly  Pro  Asp  Glu  Ala  Pro
     50                       55                      60

Arg  Met  Pro  Glu  Ala  Ala  Pro  Pro  Val  Ala  Pro  Ala  Pro  Ala  Ala  Pro
65                            70                      75                      80

Thr  Pro  Ala  Ala  Pro  Ala  Pro  Ala  Pro  Ser  Trp  Pro  Leu  Ser  Ser  Ser
               85                  90                      95

Val  Pro  Ser  Gln  Lys  Thr  Tyr  Gln  Gly  Ser  Tyr  Gly  Phe  Arg  Leu  Gly
               100                 105                     110

Phe  Leu  His  Ser  Gly  Thr  Ala  Lys  Ser  Val  Thr  Cys  Thr  Tyr  Ser  Pro
               115                 120                     125

Ala  Leu  Asn  Lys  Met  Phe  Cys  Gln  Leu  Ala  Lys  Thr  Cys  Pro  Val  Gln
               130                 135                     140

Leu  Trp  Val  Asp  Ser  Thr  Pro  Pro  Pro  Gly  Thr  Arg  Val  Arg  Ala  Met
145                      150                      155                     160

Ala  Ile  Tyr  Lys  Gln  Ser  Gln  His  Met  Thr  Glu  Val  Val  Arg  Arg  Cys
                    165                      170                     175

Pro  His  His  Glu  Arg  Cys  Ser  Asp  Ser  Asp  Gly  Leu  Ala  Pro  Pro  Gln
               180                 185                     190

His  Leu  Ile  Arg  Val  Glu  Gly  Asn  Leu  Arg  Val  Glu  Tyr  Leu  Asp  Asp
               195                 200                     205
```

```
Arg  Asn  Thr  Phe  Arg  His  Ser  Val  Val  Val  Pro  Tyr  Glu  Pro  Pro  Glu
     210                      215                      220

Val  Gly  Ser  Asp  Cys  Thr  Thr  Ile  His  Tyr  Asn  Tyr  Met  Cys  Asn  Ser
225                      230                      235                      240

Ser  Cys  Met  Gly  Gly  Met  Asn  Arg  Arg  Pro  Ile  Leu  Thr  Ile  Ile  Thr
               245                      250                           255

Leu  Glu  Asp  Ser  Ser  Gly  Asn  Leu  Leu  Gly  Arg  Asn  Ser  Phe  Glu  Val
               260                 265                      270

Arg  Val  Cys  Ala  Cys  Pro  Gly  Arg  Asp  Arg  Arg  Glu  Glu  Asn
          275                      280                 285

Leu  Arg  Lys  Lys  Gly  Glu  Pro  His  His  Glu  Leu  Pro  Pro  Gly  Ser  Thr
     290                      295                      300

Lys  Arg  Ala  Leu  Pro  Asn  Asn  Thr  Ser  Ser  Ser  Pro  Gln  Pro  Lys  Lys
305                      310                      315                      320

Lys  Pro  Leu  Asp  Gly  Glu  Tyr  Phe  Thr  Leu  Gln  Ile  Arg  Gly  Arg  Glu
               325                      330                      335

Arg  Phe  Glu  Met  Phe  Arg  Glu  Leu  Asn  Glu  Ala  Leu  Glu  Leu  Lys  Asp
               340                      345                      350

Ala  Gln  Ala  Gly  Lys  Glu  Pro  Gly  Gly  Ser  Arg  Ala  His  Ser  Ser  His
               355                      360                      365

Leu  Lys  Ser  Lys  Lys  Gly  Gln  Ser  Thr  Ser  Arg  His  Lys  Lys  Leu  Met
     370                      375                      380

Phe  Lys  Thr  Glu  Gly  Pro  Asp  Ser  Asp
385                      390
```

(2) INFORMATION FOR SEQ ID NO:4:

(i) SEQUENCE CHARACTERISTICS:
        (A) LENGTH: 393 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met  Glu  Glu  Pro  Gln  Ser  Asp  Pro  Ser  Val  Glu  Pro  Pro  Leu  Ser  Gln
1                   5                      10                      15

Glu  Thr  Phe  Ser  Asp  Leu  Trp  Lys  Leu  Leu  Pro  Glu  Asn  Asn  Val  Leu
               20                      25                      30

Ser  Pro  Leu  Pro  Ser  Gln  Ala  Met  Asp  Asp  Leu  Met  Leu  Ser  Pro  Asp
          35                      40                      45

Asp  Ile  Glu  Gln  Trp  Phe  Thr  Glu  Asp  Pro  Gly  Pro  Asp  Glu  Ala  Pro
     50                      55                      60

Arg  Met  Pro  Glu  Ala  Ala  Pro  Pro  Val  Ala  Pro  Ala  Pro  Ala  Ala  Pro
65                       70                      75                       80

Thr  Pro  Ala  Ala  Pro  Ala  Pro  Ala  Pro  Ser  Trp  Pro  Leu  Ser  Ser  Ser
               85                      90                      95

Val  Pro  Ser  Gln  Lys  Thr  Tyr  Gln  Gly  Ser  Tyr  Gly  Phe  Arg  Leu  Gly
                    100                     105                     110

Phe  Leu  His  Ser  Gly  Thr  Ala  Lys  Ser  Val  Thr  Cys  Thr  Tyr  Ser  Pro
          115                     120                     125

Ala  Leu  Asn  Lys  Met  Phe  Cys  Gln  Leu  Ala  Lys  Thr  Cys  Pro  Val  Gln
     130                     135                     140

Leu  Trp  Val  Asp  Ser  Thr  Pro  Pro  Pro  Gly  Thr  Arg  Val  Arg  Ala  Met
145                     150                     155                      160

Ala  Ile  Tyr  Lys  Gln  Ser  Gln  His  Met  Thr  Glu  Val  Val  Arg  Arg  Cys
```

|       |       |       |       |       |       |       |       |       |       |       |       |       |       |       |
|-------|-------|-------|-------|-------|-------|-------|-------|-------|-------|-------|-------|-------|-------|-------|
|       |       |       | 165   |       |       |       |       | 170   |       |       |       |       | 175   |       |
| Pro   | His   | His   | Glu   | Arg   | Cys   | Ser   | Asp   | Ser   | Asp   | Gly   | Leu   | Ala   | Pro   | Pro   | Gln |
|       |       |       | 180   |       |       |       |       | 185   |       |       |       |       | 190   |       |
| His   | Leu   | Ile   | Arg   | Val   | Glu   | Gly   | Asn   | Leu   | Arg   | Val   | Glu   | Tyr   | Leu   | Asp   | Asp |
|       |       |       | 195   |       |       |       |       | 200   |       |       |       |       | 205   |       |
| Arg   | Asn   | Thr   | Phe   | Arg   | His   | Ser   | Val   | Val   | Val   | Pro   | Tyr   | Glu   | Pro   | Pro   | Glu |
|       |       | 210   |       |       |       |       | 215   |       |       |       |       | 220   |       |       |
| Val   | Gly   | Ser   | Asp   | Cys   | Thr   | Thr   | Ile   | His   | Tyr   | Asn   | Tyr   | Met   | Cys   | Asn   | Ser |
| 225   |       |       |       |       | 230   |       |       |       |       | 235   |       |       |       |       | 240 |
| Ser   | Cys   | Met   | Gly   | Gly   | Met   | Asn   | Arg   | Arg   | Pro   | Ile   | Leu   | Thr   | Ile   | Ile   | Thr |
|       |       |       |       | 245   |       |       |       |       | 250   |       |       |       |       | 255   |     |
| Leu   | Glu   | Asp   | Ser   | Ser   | Gly   | Asn   | Leu   | Leu   | Gly   | Arg   | Asn   | Ser   | Phe   | Glu   | Val |
|       |       |       | 260   |       |       |       |       | 265   |       |       |       |       | 270   |       |     |
| Arg   | Val   | Cys   | Ala   | Cys   | Pro   | Gly   | Arg   | Asp   | Arg   | Arg   | Lys   | Glu   | Glu   | Glu   | Asn |
|       |       | 275   |       |       |       |       | 280   |       |       |       |       | 285   |       |       |     |
| Leu   | Arg   | Lys   | Lys   | Gly   | Glu   | Pro   | His   | His   | Glu   | Leu   | Pro   | Pro   | Gly   | Ser   | Thr |
|       | 290   |       |       |       |       |       | 295   |       |       |       | 300   |       |       |       |     |
| Lys   | Arg   | Ala   | Leu   | Pro   | Asn   | Asn   | Thr   | Ser   | Ser   | Ser   | Pro   | Gln   | Pro   | Lys   | Lys |
| 305   |       |       |       |       | 310   |       |       |       |       | 315   |       |       |       |       | 320 |
| Lys   | Pro   | Leu   | Asp   | Gly   | Glu   | Tyr   | Phe   | Thr   | Leu   | Gln   | Ile   | Arg   | Gly   | Arg   | Glu |
|       |       |       |       | 325   |       |       |       |       | 330   |       |       |       |       | 335   |     |
| Arg   | Phe   | Glu   | Met   | Phe   | Arg   | Glu   | Leu   | Asn   | Glu   | Ala   | Leu   | Glu   | Leu   | Lys   | Asp |
|       |       |       | 340   |       |       |       |       | 345   |       |       |       |       | 350   |       |     |
| Ala   | Gln   | Ala   | Gly   | Lys   | Glu   | Pro   | Gly   | Gly   | Ser   | Arg   | Ala   | His   | Ser   | Ser   | His |
|       |       | 355   |       |       |       |       | 360   |       |       |       |       | 365   |       |       |     |
| Leu   | Lys   | Ser   | Lys   | Lys   | Gly   | Gln   | Ser   | Thr   | Ser   | Arg   | His   | Lys   | Lys   | Leu   | Met |
|       | 370   |       |       |       |       |       | 375   |       |       |       | 380   |       |       |       |     |
| Phe   | Lys   | Thr   | Glu   | Gly   | Pro   | Asp   | Ser   | Asp   |       |       |       |       |       |       |     |
| 385   |       |       |       |       | 390   |       |       |       |       |       |       |       |       |       |     |

( 2 ) INFORMATION FOR SEQ ID NO:5:

( i ) SEQUENCE CHARACTERISTICS:
        ( A ) LENGTH: 1824 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 778..1620

( i x ) FEATURE:
        ( A ) NAME/KEY: mat_peptide
        ( B ) LOCATION: 778

( x i ) SEQUENCE DESCRIPTION: SEQ ID NO:5:

| ATCTTCGGGG | ATATAAAGTG | CATGAGCATA | CATCTTGAAA | AAAAAGATG | AAAAATTTCC | 60  |
|------------|------------|------------|------------|-----------|------------|-----|
| GACTTTAAAT | ACGGAAGATA | AATACTCCAA | CCTTTTTTC  | CAATTCCGAA | ATTTTAGTCT | 120 |
| TCTTTAAAGA | AGTTTCGGCT | CGCTGTCTTA | CCTTTTAAAA | TCTTCTACTT | CTTGACAGTA | 180 |
| CTTATCTTCT | TATATAATAG | ATATACAAAA | CAAAACAAAA | CAAAAACTCA | CAACACAGGT | 240 |
| TACTCTCCCC | CCTAAATTCA  | AATTTTTTTT | GCCCATCAGT | TTCACTAGCG | AATTATACAA | 300 |
| CTCACCAGCC | ACACAGCTCA | CTCATCTACT | TCGCAATCAA | AACAAAATAT | TTTATTTTAG | 360 |
| TTCAGTTTAT | TAAGTTATTA | TCAGTATCGT | ATTAAAAAAT | TAAAGATCAT | TGAAAAATGG | 420 |
| CTTGCTAAAC | CGATTATATT | TTGTTTTTAA | AGTAGATTAT | TATTAGAAAA | TTATTAAGAG | 480 |

```
AATTATGTGT TAAATTTATT GAAAGAGAAA ATTTATTTTC CCTTATTAAT TAAAGTCCTT      540

TACTTTTTTT GAAAACTGTC AGTTTTTGA  AGAGTTATTT GTTTGTTAC  CAATTGCTAT      600

CATGTACCCG TAGAATTTTA TTCAAGATGT TTCCGTAACG GTTACCTTTC TGTCAAATTA      660

TCCAGGTTTA CTCGCCAATA AAATTTCCC  TATACTATCA TTAATTAAAT CATTATTATT      720

ACTAAAGTTT TGTTTACCAA TTTGTCTGCT CAAGAAAATA AATTAAATAC AAATAAA        777
```

| ATG | TCC | GAA | TAT | CAG | CCA | AGT | TTA | TTT | GCT | TTA | AAT | CCA | ATG | GGT | TTC | 825 |
|---|---|---|---|---|---|---|---|---|---|---|---|---|---|---|---|---|
| Met | Ser | Glu | Tyr | Gln | Pro | Ser | Leu | Phe | Ala | Leu | Asn | Pro | Met | Gly | Phe | |
| 1 | | | | 5 | | | | | 10 | | | | | 15 | | |

| TCA | CCA | TTG | GAT | GGT | TCT | AAA | TCA | ACC | AAC | GAA | AAT | GTA | TCT | GCT | TCC | 873 |
|---|---|---|---|---|---|---|---|---|---|---|---|---|---|---|---|---|
| Ser | Pro | Leu | Asp | Gly | Ser | Lys | Ser | Thr | Asn | Glu | Asn | Val | Ser | Ala | Ser | |
| | | | 20 | | | | 25 | | | | | 30 | | | | |

| ACT | TCT | ACT | GCC | AAA | CCA | ATG | GTT | GGC | CAA | TTG | ATT | TTT | GAT | AAA | TTC | 921 |
|---|---|---|---|---|---|---|---|---|---|---|---|---|---|---|---|---|
| Thr | Ser | Thr | Ala | Lys | Pro | Met | Val | Gly | Gln | Leu | Ile | Phe | Asp | Lys | Phe | |
| | | 35 | | | | | 40 | | | | | 45 | | | | |

| ATC | AAG | ACT | GAA | GAG | GAT | CCA | ATT | ATC | AAA | CAG | GAT | ACC | CCT | TCG | AAC | 969 |
|---|---|---|---|---|---|---|---|---|---|---|---|---|---|---|---|---|
| Ile | Lys | Thr | Glu | Glu | Asp | Pro | Ile | Ile | Lys | Gln | Asp | Thr | Pro | Ser | Asn | |
| | 50 | | | | | 55 | | | | | 60 | | | | | |

| CTT | GAT | TTT | GAT | TTT | GCT | CTT | CCA | CAA | ACG | GCA | ACT | GCA | CCT | GAT | GCC | 1017 |
|---|---|---|---|---|---|---|---|---|---|---|---|---|---|---|---|---|
| Leu | Asp | Phe | Asp | Phe | Ala | Leu | Pro | Gln | Thr | Ala | Thr | Ala | Pro | Asp | Ala | |
| 65 | | | | | 70 | | | | | 75 | | | | | 80 | |

| AAG | ACC | GTT | TTG | CCA | ATT | CCG | GAG | CTA | GAT | GAC | GCT | GTA | GTG | GAA | TCT | 1065 |
|---|---|---|---|---|---|---|---|---|---|---|---|---|---|---|---|---|
| Lys | Thr | Val | Leu | Pro | Ile | Pro | Glu | Leu | Asp | Asp | Ala | Val | Val | Glu | Ser | |
| | | | | 85 | | | | | 90 | | | | | 95 | | |

| TTC | TTT | TCG | TCA | AGC | ACT | GAT | TCA | ACT | CCA | ATG | TTT | GAG | TAT | GAA | AAC | 1113 |
|---|---|---|---|---|---|---|---|---|---|---|---|---|---|---|---|---|
| Phe | Phe | Ser | Ser | Ser | Thr | Asp | Ser | Thr | Pro | Met | Phe | Glu | Tyr | Glu | Asn | |
| | | | 100 | | | | | 105 | | | | | 110 | | | |

| CTA | GAA | GAC | AAC | TCT | AAA | GAA | TGG | ACA | TCC | TTG | TTT | GAC | AAT | GAC | ATT | 1161 |
|---|---|---|---|---|---|---|---|---|---|---|---|---|---|---|---|---|
| Leu | Glu | Asp | Asn | Ser | Lys | Glu | Trp | Thr | Ser | Leu | Phe | Asp | Asn | Asp | Ile | |
| | | | 115 | | | | | 120 | | | | | 125 | | | |

| CCA | GTT | ACC | ACT | GAC | GAT | GTT | TCA | TTG | GCT | GAT | AAG | GCA | ATT | GAA | TCC | 1209 |
|---|---|---|---|---|---|---|---|---|---|---|---|---|---|---|---|---|
| Pro | Val | Thr | Thr | Asp | Asp | Val | Ser | Leu | Ala | Asp | Lys | Ala | Ile | Glu | Ser | |
| | 130 | | | | | 135 | | | | | 140 | | | | | |

| ACT | GAA | GAA | GTT | TCT | CTG | GTA | CCA | TCC | AAT | CTG | GAA | GTC | TCG | ACA | ACT | 1257 |
|---|---|---|---|---|---|---|---|---|---|---|---|---|---|---|---|---|
| Thr | Glu | Glu | Val | Ser | Leu | Val | Pro | Ser | Asn | Leu | Glu | Val | Ser | Thr | Thr | |
| 145 | | | | | 150 | | | | | 155 | | | | | 160 | |

| TCA | TTC | TTA | CCC | ACT | CCT | GTT | CTA | GAA | GAT | GCT | AAA | CTG | ACT | CAA | ACA | 1305 |
|---|---|---|---|---|---|---|---|---|---|---|---|---|---|---|---|---|
| Ser | Phe | Leu | Pro | Thr | Pro | Val | Leu | Glu | Asp | Ala | Lys | Leu | Thr | Gln | Thr | |
| | | | | 165 | | | | | 170 | | | | | 175 | | |

| AGA | AAG | GTT | AAG | AAA | CCA | AAT | TCA | GTC | GTT | AAG | AAG | TCA | CAT | CAT | GTT | 1353 |
|---|---|---|---|---|---|---|---|---|---|---|---|---|---|---|---|---|
| Arg | Lys | Val | Lys | Lys | Pro | Asn | Ser | Val | Val | Lys | Lys | Ser | His | His | Val | |
| | | | 180 | | | | | 185 | | | | | 190 | | | |

| GGA | AAG | GAT | GAC | GAA | TCG | AGA | CTG | GAT | CAT | CTA | GGT | GTT | GTT | GCT | TAC | 1401 |
|---|---|---|---|---|---|---|---|---|---|---|---|---|---|---|---|---|
| Gly | Lys | Asp | Asp | Glu | Ser | Arg | Leu | Asp | His | Leu | Gly | Val | Val | Ala | Tyr | |
| | | | 195 | | | | | 200 | | | | | 205 | | | |

| AAC | CGC | AAA | CAG | CGT | TCG | ATT | CCA | CTT | TCT | CCA | ATT | GTG | CCC | GAA | TCC | 1449 |
|---|---|---|---|---|---|---|---|---|---|---|---|---|---|---|---|---|
| Asn | Arg | Lys | Gln | Arg | Ser | Ile | Pro | Leu | Ser | Pro | Ile | Val | Pro | Glu | Ser | |
| | 210 | | | | | 215 | | | | | 220 | | | | | |

| AGT | GAT | CCT | GCT | GCT | CTA | AAA | CGT | GCT | AGA | AAC | ACT | GAA | GCC | GCC | AGG | 1497 |
|---|---|---|---|---|---|---|---|---|---|---|---|---|---|---|---|---|
| Ser | Asp | Pro | Ala | Ala | Leu | Lys | Arg | Ala | Arg | Asn | Thr | Glu | Ala | Ala | Arg | |
| 225 | | | | | 230 | | | | | 235 | | | | | 240 | |

| CGT | TCT | CGT | GCG | AGA | AAG | TTG | CAA | AGA | ATG | AAA | CAA | CTT | GAA | GAC | AAG | 1545 |
|---|---|---|---|---|---|---|---|---|---|---|---|---|---|---|---|---|
| Arg | Ser | Arg | Ala | Arg | Lys | Leu | Gln | Arg | Met | Lys | Gln | Leu | Glu | Asp | Lys | |
| | | | | 245 | | | | | 250 | | | | | 255 | | |

| GTT | GAA | GAA | TTG | CTT | TCG | AAA | AAT | TAT | CAC | TTG | GAA | AAT | GAG | GTT | GCC | 1593 |
|---|---|---|---|---|---|---|---|---|---|---|---|---|---|---|---|---|
| Val | Glu | Glu | Leu | Leu | Ser | Lys | Asn | Tyr | His | Leu | Glu | Asn | Glu | Val | Ala | |
| | | | 260 | | | | | 265 | | | | | 270 | | | |

| AGA | TTA | AAG | AAA | TTA | GTT | GGC | GAA | CGC | TGATTTCATT TACCTTTTAT | 1640 |
|---|---|---|---|---|---|---|---|---|---|---|
| Arg | Leu | Lys | Lys | Leu | Val | Gly | Glu | Arg | | |

```
Arg  Leu  Lys  Lys  Leu  Val  Gly  Glu  Arg
          275                      280
```

```
TTTATATTTT  TTATTTCATT  CTCGTGTATA  ACGAAATAGA  TACATTCACT  TAGATAAGAA    1700

TTTAATCTTT  TTTATGCCAA  TTTTCTTAAG  TAGAATTTTA  CACCACGCAT  TTATAATCTG    1760

CCGTATGTTC  TGGTATTTAC  TGGTTAGGAA  TAGATAAAAA  AAACACTCAC  GATGGGGGTC    1820

GAAC                                                                      1824
```

(2) INFORMATION FOR SEQ ID NO:6:

(i) SEQUENCE CHARACTERISTICS:
        (A) LENGTH: 281 amino acids
        (B) TYPE: amino acid
        (D) TOPOLOGY: linear (ii) MOLECULE TYPE: protein (xi) SEQUENCE DESCRIPTION: SEQ ID NO:6:

```
Met  Ser  Glu  Tyr  Gln  Pro  Ser  Leu  Phe  Ala  Leu  Asn  Pro  Met  Gly  Phe
 1                    5                        10                       15

Ser  Pro  Leu  Asp  Gly  Ser  Lys  Ser  Thr  Asn  Glu  Asn  Val  Ser  Ala  Ser
               20                       25                       30

Thr  Ser  Thr  Ala  Lys  Pro  Met  Val  Gly  Gln  Leu  Ile  Phe  Asp  Lys  Phe
               35                       40                       45

Ile  Lys  Thr  Glu  Glu  Asp  Pro  Ile  Ile  Lys  Gln  Asp  Thr  Pro  Ser  Asn
      50                       55                       60

Leu  Asp  Phe  Asp  Phe  Ala  Leu  Pro  Gln  Thr  Ala  Thr  Ala  Pro  Asp  Ala
 65                       70                       75                       80

Lys  Thr  Val  Leu  Pro  Ile  Pro  Glu  Leu  Asp  Asp  Ala  Val  Val  Glu  Ser
               85                       90                       95

Phe  Phe  Ser  Ser  Ser  Thr  Asp  Ser  Thr  Pro  Met  Phe  Glu  Tyr  Glu  Asn
              100                      105                      110

Leu  Glu  Asp  Asn  Ser  Lys  Glu  Trp  Thr  Ser  Leu  Phe  Asp  Asn  Asp  Ile
              115                      120                      125

Pro  Val  Thr  Thr  Asp  Asp  Val  Ser  Leu  Ala  Asp  Lys  Ala  Ile  Glu  Ser
              130                      135                      140

Thr  Glu  Glu  Val  Ser  Leu  Val  Pro  Ser  Asn  Leu  Glu  Val  Ser  Thr  Thr
145                      150                      155                      160

Ser  Phe  Leu  Pro  Thr  Pro  Val  Leu  Glu  Asp  Ala  Lys  Leu  Thr  Gln  Thr
              165                      170                      175

Arg  Lys  Val  Lys  Lys  Pro  Asn  Ser  Val  Val  Lys  Lys  Ser  His  His  Val
              180                      185                      190

Gly  Lys  Asp  Asp  Glu  Ser  Arg  Leu  Asp  His  Leu  Gly  Val  Val  Ala  Tyr
              195                      200                      205

Asn  Arg  Lys  Gln  Arg  Ser  Ile  Pro  Leu  Ser  Pro  Ile  Val  Pro  Glu  Ser
      210                      215                      220

Ser  Asp  Pro  Ala  Ala  Leu  Lys  Arg  Ala  Arg  Asn  Thr  Glu  Ala  Ala  Arg
225                      230                      235                      240

Arg  Ser  Arg  Ala  Arg  Lys  Leu  Gln  Arg  Met  Lys  Gln  Leu  Glu  Asp  Lys
                         245                      250                      255

Val  Glu  Glu  Leu  Leu  Ser  Lys  Asn  Tyr  His  Leu  Glu  Asn  Glu  Val  Ala
              260                      265                      270

Arg  Leu  Lys  Lys  Leu  Val  Gly  Glu  Arg
          275                      280
```

(2) INFORMATION FOR SEQ ID NO:7:

( i ) SEQUENCE CHARACTERISTICS:
  ( A ) LENGTH: 4 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:7:

Gly Asn Pro Glu
1

( 2 ) INFORMATION FOR SEQ ID NO:8:

( i ) SEQUENCE CHARACTERISTICS:
  ( A ) LENGTH: 3 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:8:

Arg Gly Asn
1

( 2 ) INFORMATION FOR SEQ ID NO:9:

( i ) SEQUENCE CHARACTERISTICS:
  ( A ) LENGTH: 6 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:9:

Arg Gly Gly Asn Pro Glu
1               5

( 2 ) INFORMATION FOR SEQ ID NO:10:

( i ) SEQUENCE CHARACTERISTICS:
  ( A ) LENGTH: 5 amino acids
  ( B ) TYPE: amino acid
  ( C ) STRANDEDNESS:
  ( D ) TOPOLOGY: linear ( i i ) MOLECULE TYPE: peptide ( x i ) SEQUENCE DESCRIPTION: SEQ ID NO:10:

Gly Gly Asn Gln Ala
1               5

( 2 ) INFORMATION FOR SEQ ID NO:11:

( i ) SEQUENCE CHARACTERISTICS:
  ( A ) LENGTH: 393 amino acids
  ( B ) TYPE: amino acid
  ( C ) STRANDEDNESS:
  ( D ) TOPOLOGY: linear ( i i ) MOLECULE TYPE: protein ( x i ) SEQUENCE DESCRIPTION: SEQ ID NO:11:

Met Glu Glu Pro Gln Ser Asp Pro Ser Val Glu Pro Pro Leu Ser Gln
1               5                   10                  15
Glu Thr Phe Ser Asp Leu Trp Lys Leu Leu Pro Glu Asn Asn Val Leu
            20                  25                  30

```
Ser  Pro  Leu  Pro  Ser  Gln  Ala  Met  Asp  Asp  Leu  Met  Leu  Ser  Pro  Asp
          35                       40                 45

Asp  Ile  Glu  Gln  Trp  Phe  Thr  Glu  Asp  Pro  Gly  Pro  Asp  Glu  Ala  Pro
     50                       55                      60

Arg  Met  Pro  Glu  Ala  Ala  Pro  Pro  Val  Ala  Pro  Ala  Pro  Ala  Ala  Pro
65                       70                       75                           80

Thr  Pro  Ala  Ala  Pro  Ala  Pro  Ala  Pro  Ser  Trp  Pro  Leu  Ser  Ser  Ser
                    85                       90                      95

Val  Pro  Ser  Gln  Lys  Thr  Tyr  Gln  Gly  Ser  Tyr  Gly  Phe  Arg  Leu  Gly
                    100                      105                     110

Phe  Leu  His  Ser  Gly  Thr  Ala  Lys  Ser  Val  Thr  Cys  Thr  Tyr  Ser  Pro
               115                      120                     125

Ala  Leu  Asn  Lys  Met  Phe  Cys  Gln  Leu  Ala  Lys  Thr  Cys  Pro  Val  Gln
          130                      135                     140

Leu  Trp  Val  Asp  Ser  Thr  Pro  Pro  Gly  Thr  Arg  Val  Arg  Ala  Met
145                      150                      155                          160

Ala  Ile  Tyr  Lys  Gln  Ser  Gln  His  Met  Thr  Glu  Val  Val  Arg  Arg  Cys
                    165                      170                     175

Pro  His  His  Glu  Arg  Cys  Ser  Asp  Ser  Asp  Gly  Leu  Ala  Pro  Pro  Gln
               180                      185                     190

His  Leu  Ile  Arg  Val  Glu  Gly  Asn  Leu  Arg  Val  Glu  Tyr  Leu  Asp  Asp
               195                      200                     205

Arg  Asn  Thr  Phe  Arg  His  Ser  Val  Val  Val  Pro  Tyr  Glu  Pro  Pro  Glu
     210                      215                      220

Val  Gly  Ser  Asp  Cys  Thr  Thr  Ile  His  Tyr  Asn  Tyr  Met  Cys  Asn  Ser
225                      230                      235                          240

Ser  Cys  Met  Gly  Gly  Met  Asn  Gln  Arg  Pro  Ile  Leu  Thr  Ile  Ile  Thr
               245                      250                     255

Leu  Glu  Asp  Ser  Ser  Gly  Asn  Leu  Leu  Gly  Arg  Asn  Ser  Phe  Glu  Val
               260                      265                     270

Arg  Val  Cys  Ala  Cys  Pro  Gly  Arg  Asp  Arg  Arg  Thr  Glu  Glu  Glu  Asn
          275                      280                     285

Leu  Arg  Lys  Lys  Gly  Glu  Pro  His  His  Glu  Leu  Pro  Pro  Gly  Ser  Thr
     290                      295                     300

Lys  Arg  Ala  Leu  Pro  Asn  Asn  Thr  Ser  Ser  Ser  Pro  Gln  Pro  Lys  Lys
305                      310                      315                          320

Lys  Pro  Leu  Asp  Gly  Glu  Tyr  Phe  Thr  Leu  Gln  Ile  Arg  Gly  Arg  Glu
                    325                      330                     335

Arg  Phe  Glu  Met  Phe  Arg  Glu  Leu  Asn  Glu  Ala  Leu  Glu  Leu  Lys  Asp
               340                      345                     350

Ala  Gln  Ala  Gly  Lys  Glu  Pro  Gly  Gly  Ser  Arg  Ala  His  Ser  Ser  His
          355                      360                     365

Leu  Lys  Ser  Lys  Lys  Gly  Gln  Ser  Thr  Ser  Arg  His  Lys  Lys  Leu  Met
     370                      375                     380

Phe  Lys  Thr  Glu  Gly  Pro  Asp  Ser  Asp
385                      390
```

( 2 ) INFORMATION FOR SEQ ID NO:12:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:12:

| Met 1 | Glu | Glu | Pro | Gln 5 | Ser | Asp | Pro | Ser | Val 10 | Glu | Pro | Pro | Leu | Ser 15 | Gln |
| Glu | Thr | Phe | Ser 20 | Asp | Leu | Trp | Lys | Leu 25 | Leu | Pro | Glu | Asn | Asn 30 | Val | Leu |
| Ser | Pro | Leu 35 | Pro | Ser | Gln | Ala | Met 40 | Asp | Asp | Leu | Met | Leu 45 | Ser | Pro | Asp |
| Asp | Ile 50 | Glu | Gln | Trp | Phe | Thr 55 | Glu | Asp | Pro | Gly | Pro 60 | Asp | Glu | Ala | Pro |
| Arg 65 | Met | Pro | Glu | Ala | Ala 70 | Pro | Pro | Val | Ala | Pro 75 | Ala | Pro | Ala | Ala | Pro 80 |
| Thr | Pro | Ala | Ala | Pro 85 | Ala | Pro | Ala | Pro | Ser 90 | Trp | Pro | Leu | Ser | Ser 95 | Ser |
| Val | Pro | Ser | Gln 100 | Lys | Thr | Tyr | Gln | Gly 105 | Ser | Tyr | Gly | Phe | Arg 110 | Leu | Gly |
| Phe | Leu | His 115 | Ser | Gly | Thr | Ala | Lys 120 | Ser | Val | Thr | Cys | Thr 125 | Tyr | Ser | Pro |
| Ala | Leu | Asn 130 | Lys | Met | Phe | Cys | Gln 135 | Leu | Ala | Lys | Thr | Cys 140 | Pro | Val | Gln |
| Leu 145 | Trp | Val | Asp | Ser | Thr 150 | Pro | Pro | Pro | Gly | Thr 155 | Arg | Val | Arg | Ala | Met 160 |
| Ala | Ile | Tyr | Lys | Gln 165 | Ser | Gln | His | Met | Thr 170 | Glu | Val | Val | Arg | Arg 175 | Cys |
| Pro | His | His | Glu 180 | Arg | Cys | Ser | Asp | Ser 185 | Asp | Gly | Leu | Ala | Pro 190 | Pro | Gln |
| His | Leu | Ile 195 | Arg | Val | Glu | Gly | Asn 200 | Leu | Arg | Val | Glu | Tyr 205 | Leu | Asp | Asp |
| Arg | Asn 210 | Thr | Phe | Arg | His | Ser 215 | Val | Val | Val | Pro | Tyr 220 | Glu | Pro | Pro | Glu |
| Val 225 | Gly | Ser | Asp | Cys | Thr 230 | Thr | Ile | His | Tyr | Asn 235 | Tyr | Met | Cys | Asn | Ser 240 |
| Ser | Cys | Met | Gly | Gly 245 | Met | Asn | Arg | Arg | Pro 250 | Ile | Leu | Thr | Ile | Ile 255 | Thr |
| Leu | Glu | Asp | Ser 260 | Ser | Gly | Asn | Leu | Leu 265 | Gly | Arg | Asn | Ser | Phe 270 | Glu | Val |
| His | Val | Cys 275 | Ala | Cys | Pro | Gly | Arg 280 | Asp | Arg | Arg | Thr | Glu 285 | Glu | Glu | Asn |
| Leu | Arg 290 | Lys | Lys | Gly | Glu | Pro 295 | His | His | Glu | Leu | Pro 300 | Pro | Gly | Ser | Thr |
| Lys 305 | Arg | Ala | Leu | Pro | Asn 310 | Asn | Thr | Ser | Ser | Ser 315 | Pro | Gln | Pro | Lys | Lys 320 |
| Lys | Pro | Leu | Asp | Gly 325 | Glu | Tyr | Phe | Thr | Leu 330 | Gln | Ile | Arg | Gly | Arg 335 | Glu |
| Arg | Phe | Glu | Met 340 | Phe | Arg | Glu | Leu | Asn 345 | Glu | Ala | Leu | Glu | Leu 350 | Lys | Asp |
| Ala | Gln | Ala 355 | Gly | Lys | Glu | Pro | Gly 360 | Gly | Ser | Arg | Ala | His 365 | Ser | Ser | His |
| Leu | Lys 370 | Ser | Lys | Lys | Gly | Gln 375 | Ser | Thr | Ser | Arg | His 380 | Lys | Lys | Leu | Met |
| Phe 385 | Lys | Thr | Glu | Gly | Pro 390 | Asp | Ser | Asp | | | | | | | |

( 2 ) INFORMATION FOR SEQ ID NO:13:

( i ) SEQUENCE CHARACTERISTICS:
- ( A ) LENGTH: 393 amino acids
- ( B ) TYPE: amino acid
- ( C ) STRANDEDNESS:
- ( D ) TOPOLOGY: linear ( i i ) MOLECULE TYPE: protein ( x i ) SEQUENCE DESCRIPTION: SEQ ID NO:13:

```
Met  Glu  Glu  Pro  Gln  Ser  Asp  Pro  Ser  Val  Glu  Pro  Pro  Leu  Ser  Gln
1              5                        10                       15

Glu  Thr  Phe  Ser  Asp  Leu  Trp  Lys  Leu  Leu  Pro  Glu  Asn  Asn  Val  Leu
               20                       25                  30

Ser  Pro  Leu  Pro  Ser  Gln  Ala  Met  Asp  Asp  Leu  Met  Leu  Ser  Pro  Asp
          35                       40                  45

Asp  Ile  Glu  Gln  Trp  Phe  Thr  Glu  Asp  Pro  Gly  Pro  Asp  Glu  Ala  Pro
     50                       55                  60

Arg  Met  Pro  Glu  Ala  Ala  Pro  Pro  Val  Ala  Pro  Ala  Pro  Ala  Ala  Pro
65                       70                  75                            80

Thr  Pro  Ala  Ala  Pro  Ala  Pro  Ala  Pro  Ser  Trp  Pro  Leu  Ser  Ser  Ser
               85                       90                       95

Val  Pro  Ser  Gln  Lys  Thr  Tyr  Gln  Gly  Ser  Tyr  Gly  Phe  Arg  Leu  Gly
                    100                      105                 110

Phe  Leu  His  Ser  Gly  Thr  Ala  Lys  Ser  Val  Thr  Cys  Thr  Tyr  Ser  Pro
               115                      120                 125

Ala  Leu  Asn  Lys  Met  Phe  Cys  Gln  Leu  Ala  Lys  Thr  Cys  Pro  Val  Gln
          130                      135                 140

Leu  Trp  Val  Asp  Ser  Thr  Pro  Pro  Pro  Gly  Thr  Arg  Val  Arg  Ala  Met
145                      150                      155                      160

Ala  Ile  Tyr  Lys  Gln  Ser  Gln  His  Met  Thr  Glu  Val  Val  Arg  Arg  Cys
                    165                      170                 175

Pro  His  His  Glu  Arg  Cys  Ser  Asp  Ser  Asp  Gly  Leu  Ala  Pro  Pro  Gln
               180                      185                 190

His  Leu  Ile  Arg  Val  Glu  Gly  Asn  Leu  Arg  Val  Glu  Tyr  Leu  Asp  Asp
          195                      200                 205

Arg  Asn  Thr  Phe  Arg  His  Ser  Val  Val  Val  Pro  Tyr  Glu  Pro  Pro  Glu
     210                      215                 220

Val  Gly  Ser  Asp  Cys  Thr  Thr  Ile  His  Tyr  Asn  Tyr  Met  Cys  Asn  Ser
225                      230                      235                      240

Ser  Cys  Met  Gly  Gly  Met  Asn  Arg  Arg  Pro  Ile  Leu  Thr  Ile  Ile  Thr
                    245                      250                 255

Leu  Glu  Asp  Ser  Ser  Gly  Asn  Leu  Leu  Gly  Arg  Asn  Ser  Phe  Glu  Val
               260                      265                 270

Cys  Val  Cys  Ala  Cys  Pro  Gly  Arg  Asp  Arg  Arg  Thr  Glu  Glu  Glu  Asn
          275                      280                 285

Leu  Arg  Lys  Lys  Gly  Glu  Pro  His  His  Glu  Leu  Pro  Pro  Gly  Ser  Thr
     290                      295                 300

Lys  Arg  Ala  Leu  Pro  Asn  Asn  Thr  Ser  Ser  Ser  Pro  Gln  Pro  Lys  Lys
305                      310                      315                      320

Lys  Pro  Leu  Asp  Gly  Glu  Tyr  Phe  Thr  Leu  Gln  Ile  Arg  Gly  Arg  Glu
                    325                      330                 335

Arg  Phe  Glu  Met  Phe  Arg  Glu  Leu  Asn  Glu  Ala  Leu  Glu  Leu  Lys  Asp
               340                      345                 350

Ala  Gln  Ala  Gly  Lys  Glu  Pro  Gly  Gly  Ser  Arg  Ala  His  Ser  Ser  His
          355                      360                 365

Leu  Lys  Ser  Lys  Lys  Gly  Gln  Ser  Thr  Ser  Arg  His  Lys  Lys  Leu  Met
```

370                        375                         380

Phe   Lys   Thr   Glu   Gly   Pro   Asp   Ser   Asp
        385                           390

(2) INFORMATION FOR SEQ ID NO:14:

(i) SEQUENCE CHARACTERISTICS:
        (A) LENGTH: 393 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met   Glu   Glu   Pro   Gln   Ser   Asp   Pro   Ser   Val   Glu   Pro   Pro   Leu   Ser   Gln
        1                       5                       10                          15

Glu   Thr   Phe   Ser   Asp   Leu   Trp   Lys   Leu   Leu   Pro   Glu   Asn   Asn   Val   Leu
                          20                      25                          30

Ser   Pro   Leu   Pro   Ser   Gln   Ala   Met   Asp   Asp   Leu   Met   Leu   Ser   Pro   Asp
                          35                      40                          45

Asp   Ile   Glu   Gln   Trp   Phe   Thr   Glu   Asp   Pro   Gly   Pro   Asp   Glu   Ala   Pro
                    50                      55                          60

Arg   Met   Pro   Glu   Ala   Ala   Pro   Pro   Val   Ala   Pro   Ala   Pro   Ala   Ala   Pro
        65                            70                          75                            80

Thr   Pro   Ala   Ala   Pro   Ala   Pro   Ala   Pro   Ser   Trp   Pro   Leu   Ser   Ser   Ser
                                85                      90                          95

Val   Pro   Ser   Gln   Lys   Thr   Tyr   Gln   Gly   Ser   Tyr   Gly   Phe   Arg   Leu   Gly
                          100                     105                         110

Phe   Leu   His   Ser   Gly   Thr   Ala   Lys   Ser   Val   Thr   Cys   Thr   Tyr   Ser   Pro
                    115                     120                         125

Ala   Leu   Asn   Lys   Met   Phe   Cys   Gln   Leu   Ala   Lys   Thr   Cys   Pro   Val   Gln
                    130                     135                         140

Leu   Trp   Val   Asp   Ser   Thr   Pro   Pro   Gly   Thr   Arg   Val   Arg   Ala   Met
        145                           150                         155                           160

Ala   Ile   Tyr   Lys   Gln   Ser   Gln   His   Met   Thr   Glu   Val   Val   Arg   Arg   Cys
                          165                     170                         175

Pro   His   His   Glu   Arg   Cys   Ser   Asp   Ser   Asp   Gly   Leu   Ala   Pro   Pro   Gln
                          180                     185                         190

His   Leu   Ile   Arg   Val   Glu   Gly   Asn   Leu   Arg   Val   Glu   Tyr   Leu   Asp   Asp
                    195                     200                         205

Arg   Asn   Thr   Phe   Arg   His   Ser   Val   Val   Val   Pro   Tyr   Glu   Pro   Pro   Glu
              210                     215                         220

Val   Gly   Ser   Asp   Cys   Thr   Thr   Ile   His   Tyr   Asn   Tyr   Met   Cys   Asn   Ser
        225                           230                         235                           240

Ser   Cys   Met   Gly   Gly   Met   Asn   Gln   Arg   Pro   Ile   Leu   Thr   Ile   Ile   Thr
                                245                     250                         255

Leu   Glu   Asp   Ser   Ser   Gly   Asn   Leu   Leu   Gly   Arg   Asn   Ser   Phe   Glu   Val
                          260                     265                         270

Arg   Val   Cys   Ala   Cys   Pro   Gly   Arg   Asp   Arg   Arg   Glu   Glu   Asn
                          275                     280                         285

Leu   Arg   Lys   Lys   Gly   Glu   Pro   His   His   Glu   Leu   Pro   Pro   Gly   Ser   Thr
              290                     295                         300

Lys   Arg   Ala   Leu   Pro   Asn   Asn   Thr   Ser   Ser   Ser   Pro   Gln   Pro   Lys   Lys
        305                           310                         315                           320

Lys   Pro   Leu   Asp   Gly   Glu   Tyr   Phe   Thr   Leu   Gln   Ile   Arg   Gly   Arg   Glu
                          325                     330                         335

|     |     |     |     |     |     |     |     |     |     |     |     |     |     |     |
|-----|-----|-----|-----|-----|-----|-----|-----|-----|-----|-----|-----|-----|-----|-----|
| Arg | Phe | Glu | Met<br>340 | Phe | Arg | Glu | Leu | Asn<br>345 | Glu | Ala | Leu | Glu<br>350 | Leu | Lys | Asp |
| Ala | Gln | Ala<br>355 | Gly | Lys | Glu | Pro<br>360 | Gly | Gly | Ser | Arg | Ala<br>365 | His | Ser | Ser | His |
| Leu | Lys<br>370 | Ser | Lys | Lys | Gly | Gln<br>375 | Ser | Thr | Ser | Arg | His<br>380 | Lys | Lys | Leu | Met |
| Phe<br>385 | Lys | Thr | Glu | Gly | Pro<br>390 | Asp | Ser | Asp | | | | | | | |

(2) INFORMATION FOR SEQ ID NO:15:

(i) SEQUENCE CHARACTERISTICS:
        (A) LENGTH: 393 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

|     |     |     |     |     |     |     |     |     |     |     |     |     |     |     |     |
|-----|-----|-----|-----|-----|-----|-----|-----|-----|-----|-----|-----|-----|-----|-----|-----|
| Met<br>1 | Glu | Glu | Pro | Gln<br>5 | Ser | Asp | Pro | Ser | Val<br>10 | Glu | Pro | Pro | Leu | Ser<br>15 | Gln |
| Glu | Thr | Phe | Ser<br>20 | Asp | Leu | Trp | Lys<br>25 | Leu | Leu | Pro | Glu | Asn<br>30 | Asn | Val | Leu |
| Ser | Pro | Leu<br>35 | Pro | Ser | Gln | Ala | Met<br>40 | Asp | Asp | Leu | Met | Leu<br>45 | Ser | Pro | Asp |
| Asp | Ile<br>50 | Glu | Gln | Trp | Phe | Thr<br>55 | Glu | Asp | Pro | Gly | Pro<br>60 | Asp | Glu | Ala | Pro |
| Arg<br>65 | Met | Pro | Glu | Ala | Ala<br>70 | Pro | Pro | Val | Ala | Pro<br>75 | Ala | Pro | Ala | Ala<br>80 | Pro |
| Thr | Pro | Ala | Ala | Pro<br>85 | Ala | Pro | Ala | Pro | Ser<br>90 | Trp | Pro | Leu | Ser | Ser<br>95 | Ser |
| Val | Pro | Ser | Gln | Lys<br>100 | Thr | Tyr | Gln | Gly | Ser<br>105 | Tyr | Gly | Phe | Arg | Leu<br>110 | Gly |
| Phe | Leu | His<br>115 | Ser | Gly | Thr | Ala | Lys<br>120 | Ser | Val | Thr | Cys | Thr<br>125 | Tyr | Ser | Pro |
| Ala | Leu<br>130 | Asn | Lys | Met | Phe | Cys<br>135 | Gln | Leu | Ala | Lys | Thr<br>140 | Cys | Pro | Val | Gln |
| Leu<br>145 | Trp | Val | Asp | Ser | Thr<br>150 | Pro | Pro | Pro | Gly | Thr<br>155 | Arg | Val | Arg | Ala | Met<br>160 |
| Ala | Ile | Tyr | Lys | Gln<br>165 | Ser | Gln | His | Met | Thr<br>170 | Glu | Val | Val | Arg | Arg<br>175 | Cys |
| Pro | His | His | Glu<br>180 | Arg | Cys | Ser | Asp | Ser<br>185 | Asp | Gly | Leu | Ala | Pro<br>190 | Pro | Gln |
| His | Leu | Ile<br>195 | Arg | Val | Glu | Gly | Asn<br>200 | Leu | Arg | Val | Glu | Tyr<br>205 | Leu | Asp | Asp |
| Arg | Asn<br>210 | Thr | Phe | Arg | His | Ser<br>215 | Val | Val | Val | Pro | Tyr<br>220 | Glu | Pro | Pro | Glu |
| Val<br>225 | Gly | Ser | Asp | Cys | Thr<br>230 | Thr | Ile | His | Tyr | Asn<br>235 | Tyr | Met | Cys | Asn | Ser<br>240 |
| Ser | Cys | Met | Gly | Gly<br>245 | Met | Asn | Arg | Arg | Pro<br>250 | Ile | Leu | Thr | Ile | Ile<br>255 | Thr |
| Leu | Glu | Asp | Ser<br>260 | Ser | Gly | Asn | Leu | Leu<br>265 | Gly | Arg | Asn | Ser | Phe<br>270 | Glu | Val |
| His | Val | Cys<br>275 | Ala | Cys | Pro | Gly | Arg<br>280 | Asp | Arg | Arg | Arg | Glu<br>285 | Glu | Glu | Asn |

| | | | | | | | | | | | | | | |
|---|---|---|---|---|---|---|---|---|---|---|---|---|---|---|
| Leu | Arg<br>290 | Lys | Lys | Gly | Glu<br>295 | Pro | His | His | Glu | Leu<br>300 | Pro | Pro | Gly | Ser | Thr |
| Lys<br>305 | Arg | Ala | Leu | Pro<br>310 | Asn | Asn | Thr | Ser | Ser<br>315 | Pro | Gln | Pro | Lys | Lys<br>320 |
| Lys | Pro | Leu | Asp | Gly<br>325 | Glu | Tyr | Phe | Thr | Leu<br>330 | Gln | Ile | Arg | Gly | Arg<br>335 | Glu |
| Arg | Phe | Glu | Met<br>340 | Phe | Arg | Glu | Leu | Asn<br>345 | Glu | Ala | Leu | Glu | Leu<br>350 | Lys | Asp |
| Ala | Gln | Ala<br>355 | Gly | Lys | Glu | Pro | Gly<br>360 | Gly | Ser | Arg | Ala | His<br>365 | Ser | Ser | His |
| Leu | Lys<br>370 | Ser | Lys | Lys | Gly | Gln<br>375 | Ser | Thr | Ser | Arg | His<br>380 | Lys | Lys | Leu | Met |
| Phe<br>385 | Lys | Thr | Glu | Gly | Pro<br>390 | Asp | Ser | Asp |

( 2 ) INFORMATION FOR SEQ ID NO:16:

( i ) SEQUENCE CHARACTERISTICS:
    ( A ) LENGTH: 393 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Met<br>1 | Glu | Glu | Pro | Gln<br>5 | Ser | Asp | Pro | Ser | Val<br>10 | Glu | Pro | Pro | Leu | Ser<br>15 | Gln |
| Glu | Thr | Phe | Ser<br>20 | Asp | Leu | Trp | Lys | Leu<br>25 | Leu | Pro | Glu | Asn | Asn<br>30 | Val | Leu |
| Ser | Pro | Leu<br>35 | Pro | Ser | Gln | Ala | Met<br>40 | Asp | Asp | Leu | Met | Leu<br>45 | Ser | Pro | Asp |
| Asp | Ile<br>50 | Glu | Gln | Trp | Phe | Thr<br>55 | Glu | Asp | Pro | Gly | Pro<br>60 | Asp | Glu | Ala | Pro |
| Arg<br>65 | Met | Pro | Glu | Ala | Ala<br>70 | Pro | Pro | Val | Ala | Pro<br>75 | Ala | Pro | Ala | Ala | Pro<br>80 |
| Thr | Pro | Ala | Ala | Pro<br>85 | Ala | Pro | Ala | Pro | Ser<br>90 | Trp | Pro | Leu | Ser | Ser<br>95 | Ser |
| Val | Pro | Ser | Gln | Lys<br>100 | Thr | Tyr | Gln | Gly<br>105 | Ser | Tyr | Gly | Phe | Arg<br>110 | Leu | Gly |
| Phe | Leu | His | Ser<br>115 | Gly | Thr | Ala | Lys<br>120 | Ser | Val | Thr | Cys | Thr<br>125 | Tyr | Ser | Pro |
| Ala | Leu | Asn<br>130 | Lys | Met | Phe | Cys<br>135 | Gln | Leu | Ala | Lys | Thr<br>140 | Cys | Pro | Val | Gln |
| Leu<br>145 | Trp | Val | Asp | Ser | Thr<br>150 | Pro | Pro | Pro | Gly | Thr<br>155 | Arg | Val | Arg | Ala | Met<br>160 |
| Ala | Ile | Tyr | Lys | Gln<br>165 | Ser | Gln | His | Met | Thr<br>170 | Glu | Val | Val | Arg | Arg<br>175 | Cys |
| Pro | His | His | Glu<br>180 | Arg | Cys | Ser | Asp | Ser<br>185 | Asp | Gly | Leu | Ala | Pro<br>190 | Pro | Gln |
| His | Leu | Ile<br>195 | Arg | Val | Glu | Gly | Asn<br>200 | Leu | Arg | Val | Glu | Tyr<br>205 | Leu | Asp | Asp |
| Arg | Asn<br>210 | Thr | Phe | Arg | His | Ser<br>215 | Val | Val | Val | Pro | Tyr<br>220 | Glu | Pro | Pro | Glu |
| Val<br>225 | Gly | Ser | Asp | Cys | Thr<br>230 | Thr | Ile | His | Tyr | Asn<br>235 | Tyr | Met | Cys | Asn | Ser<br>240 |
| Ser | Cys | Met | Gly | Gly | Met | Asn | Arg | Arg | Pro | Ile | Leu | Thr | Ile | Ile | Thr |

|     |     |     |     | 245 |     |     |     | 250 |     |     |     | 255 |     |
|---|---|---|---|---|---|---|---|---|---|---|---|---|---|
| Leu | Glu | Asp | Ser | Ser | Gly | Asn | Leu | Leu | Gly | Arg | Asn | Ser | Phe | Glu | Val |
|     |     |     | 260 |     |     |     | 265 |     |     |     | 270 |     |     |
| Cys | Val | Cys | Ala | Cys | Pro | Gly | Arg | Asp | Arg | Arg | Glu | Glu | Asn |
|     |     | 275 |     |     |     | 280 |     |     |     | 285 |     |     |     |
| Leu | Arg | Lys | Lys | Gly | Glu | Pro | His | His | Glu | Leu | Pro | Pro | Gly | Ser | Thr |
|     | 290 |     |     |     |     | 295 |     |     |     |     | 300 |     |     |
| Lys | Arg | Ala | Leu | Pro | Asn | Asn | Thr | Ser | Ser | Ser | Pro | Gln | Pro | Lys | Lys |
| 305 |     |     |     |     | 310 |     |     |     | 315 |     |     |     |     | 320 |
| Lys | Pro | Leu | Asp | Gly | Glu | Tyr | Phe | Thr | Leu | Gln | Ile | Arg | Gly | Arg | Glu |
|     |     |     |     | 325 |     |     |     | 330 |     |     |     | 335 |     |
| Arg | Phe | Glu | Met | Phe | Arg | Glu | Leu | Asn | Glu | Ala | Leu | Glu | Leu | Lys | Asp |
|     |     |     | 340 |     |     |     | 345 |     |     |     | 350 |     |
| Ala | Gln | Ala | Gly | Lys | Glu | Pro | Gly | Gly | Ser | Arg | Ala | His | Ser | Ser | His |
|     |     | 355 |     |     |     | 360 |     |     |     | 365 |     |     |     |
| Leu | Lys | Ser | Lys | Lys | Gly | Gln | Ser | Thr | Ser | Arg | His | Lys | Lys | Leu | Met |
|     | 370 |     |     |     |     | 375 |     |     |     | 380 |     |     |     |
| Phe | Lys | Thr | Glu | Gly | Pro | Asp | Ser | Asp |
| 385 |     |     |     |     | 390 |     |     |     |

( 2 ) INFORMATION FOR SEQ ID NO:17:

( i ) SEQUENCE CHARACTERISTICS:
( A ) LENGTH: 363 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:17:

| Met | Glu | Glu | Pro | Gln | Ser | Asp | Pro | Ser | Val | Glu | Pro | Pro | Leu | Ser | Gln |
| --- | --- | --- | --- | --- | --- | --- | --- | --- | --- | --- | --- | --- | --- | --- | --- |
| 1 |  |  |  | 5 |  |  |  |  | 10 |  |  |  |  | 15 |  |
| Glu | Thr | Phe | Ser | Asp | Leu | Trp | Lys | Leu | Leu | Pro | Glu | Asn | Asn | Val | Leu |
|  |  |  | 20 |  |  |  | 25 |  |  |  |  | 30 |  |  |
| Ser | Pro | Leu | Pro | Ser | Gln | Ala | Met | Asp | Asp | Leu | Met | Leu | Ser | Pro | Asp |
|  |  | 35 |  |  |  | 40 |  |  |  |  | 45 |  |  |  |
| Asp | Ile | Glu | Gln | Trp | Phe | Thr | Glu | Asp | Pro | Gly | Pro | Asp | Glu | Ala | Pro |
|  | 50 |  |  |  |  | 55 |  |  |  |  | 60 |  |  |  |
| Arg | Met | Pro | Glu | Ala | Ala | Pro | Pro | Val | Ala | Pro | Ala | Pro | Ala | Ala | Pro |
| 65 |  |  |  |  | 70 |  |  |  |  | 75 |  |  |  |  | 80 |
| Thr | Pro | Ala | Ala | Pro | Ala | Pro | Ala | Pro | Ser | Trp | Pro | Leu | Ser | Ser | Ser |
|  |  |  |  | 85 |  |  |  |  | 90 |  |  |  |  | 95 |
| Val | Pro | Ser | Gln | Lys | Thr | Tyr | Gln | Gly | Ser | Tyr | Gly | Phe | Arg | Leu | Gly |
|  |  |  | 100 |  |  |  | 105 |  |  |  |  | 110 |  |  |
| Phe | Leu | His | Ser | Gly | Thr | Ala | Lys | Ser | Val | Thr | Cys | Thr | Tyr | Ser | Pro |
|  |  | 115 |  |  |  | 120 |  |  |  |  | 125 |  |  |  |
| Ala | Leu | Asn | Lys | Met | Phe | Cys | Gln | Leu | Ala | Lys | Thr | Cys | Pro | Val | Gln |
|  | 130 |  |  |  |  | 135 |  |  |  |  | 140 |  |  |  |
| Leu | Trp | Val | Asp | Ser | Thr | Pro | Pro | Pro | Gly | Thr | Arg | Val | Arg | Ala | Met |
| 145 |  |  |  |  | 150 |  |  |  |  | 155 |  |  |  |  | 160 |
| Ala | Ile | Tyr | Lys | Gln | Ser | Gln | His | Met | Thr | Glu | Val | Val | Arg | Arg | Cys |
|  |  |  |  | 165 |  |  |  | 170 |  |  |  |  | 175 |
| Pro | His | His | Glu | Arg | Cys | Ser | Asp | Ser | Asp | Gly | Leu | Ala | Pro | Pro | Gln |
|  |  |  | 180 |  |  |  | 185 |  |  |  |  | 190 |  |  |
| His | Leu | Ile | Arg | Val | Glu | Gly | Asn | Leu | Arg | Val | Glu | Tyr | Leu | Asp | Asp |
|  |  | 195 |  |  |  | 200 |  |  |  |  | 205 |  |  |  |

| Arg | Asn | Thr | Phe | Arg | His | Ser | Val | Val | Pro | Tyr | Glu | Pro | Pro | Glu |
|---|---|---|---|---|---|---|---|---|---|---|---|---|---|---|
| 210 | | | | | 215 | | | | | 220 | | | | |
| Val | Gly | Ser | Asp | Cys | Thr | Thr | Ile | His | Tyr | Asn | Tyr | Met | Cys | Asn | Ser |
| 225 | | | | | 230 | | | | | 235 | | | | | 240 |
| Ser | Cys | Met | Gly | Gly | Met | Asn | Arg | Arg | Pro | Ile | Leu | Thr | Ile | Ile | Thr |
| | | | | 245 | | | | | 250 | | | | | 255 | |
| Leu | Glu | Asp | Ser | Ser | Gly | Asn | Leu | Leu | Gly | Arg | Asn | Ser | Phe | Glu | Val |
| | | | 260 | | | | | 265 | | | | | 270 | | |
| Arg | Val | Cys | Ala | Cys | Pro | Gly | Arg | Asp | Arg | Arg | Thr | Glu | Glu | Asn |
| | | 275 | | | | | 280 | | | | | 285 | | |
| Leu | Arg | Lys | Lys | Gly | Glu | Pro | His | His | Glu | Leu | Pro | Pro | Gly | Ser | Thr |
| | 290 | | | | | 295 | | | | | 300 | | | | |
| Lys | Arg | Ala | Leu | Pro | Asn | Asn | Thr | Ser | Ser | Ser | Pro | Gln | Pro | Lys | Lys |
| 305 | | | | | 310 | | | | | 315 | | | | | 320 |
| Lys | Pro | Leu | Asp | Gly | Glu | Tyr | Phe | Thr | Leu | Gln | Ile | Arg | Gly | Arg | Glu |
| | | | | 325 | | | | | 330 | | | | | 335 | |
| Arg | Phe | Glu | Met | Phe | Arg | Glu | Leu | Asn | Glu | Ala | Leu | Glu | Leu | Lys | Asp |
| | | | 340 | | | | | 345 | | | | | 350 | | |
| Ala | Gln | Ala | Gly | Lys | Glu | Pro | Gly | Gly | Ser | Arg |
| | | | 355 | | | | 360 | | | |

(2) INFORMATION FOR SEQ ID NO:18:

(i) SEQUENCE CHARACTERISTICS:
        (A) LENGTH: 363 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

| Met | Glu | Glu | Pro | Gln | Ser | Asp | Pro | Ser | Val | Glu | Pro | Pro | Leu | Ser | Gln |
|---|---|---|---|---|---|---|---|---|---|---|---|---|---|---|---|
| 1 | | | | 5 | | | | | 10 | | | | | 15 | |
| Glu | Thr | Phe | Ser | Asp | Leu | Trp | Lys | Leu | Leu | Pro | Glu | Asn | Asn | Val | Leu |
| | | | 20 | | | | | 25 | | | | | 30 | | |
| Ser | Pro | Leu | Pro | Ser | Gln | Ala | Met | Asp | Asp | Leu | Met | Leu | Ser | Pro | Asp |
| | | 35 | | | | | 40 | | | | | 45 | | | |
| Asp | Ile | Glu | Gln | Trp | Phe | Thr | Glu | Asp | Pro | Gly | Pro | Asp | Glu | Ala | Pro |
| 50 | | | | | 55 | | | | | 60 | | | | | |
| Arg | Met | Pro | Glu | Ala | Ala | Pro | Pro | Val | Ala | Pro | Ala | Pro | Ala | Ala | Pro |
| 65 | | | | | 70 | | | | | 75 | | | | | 80 |
| Thr | Pro | Ala | Ala | Pro | Ala | Pro | Ala | Pro | Ser | Trp | Pro | Leu | Ser | Ser | Ser |
| | | | | 85 | | | | | 90 | | | | | 95 | |
| Val | Pro | Ser | Gln | Lys | Thr | Tyr | Gln | Gly | Ser | Tyr | Gly | Phe | Arg | Leu | Gly |
| | | | | 100 | | | | | 105 | | | | | 110 | |
| Phe | Leu | His | Ser | Gly | Thr | Ala | Lys | Ser | Val | Thr | Cys | Thr | Tyr | Ser | Pro |
| | | | 115 | | | | | 120 | | | | | 125 | | |
| Ala | Leu | Asn | Lys | Met | Phe | Cys | Gln | Leu | Ala | Lys | Thr | Cys | Pro | Val | Gln |
| | | | 130 | | | | | 135 | | | | | 140 | | |
| Leu | Trp | Val | Asp | Ser | Thr | Pro | Pro | Pro | Gly | Thr | Arg | Val | Arg | Ala | Met |
| 145 | | | | | 150 | | | | | 155 | | | | | 160 |
| Ala | Ile | Tyr | Lys | Gln | Ser | Gln | His | Met | Thr | Glu | Val | Val | Arg | Arg | Cys |
| | | | | 165 | | | | | 170 | | | | | 175 | |
| Pro | His | His | Glu | Arg | Cys | Ser | Asp | Ser | Asp | Gly | Leu | Ala | Pro | Pro | Gln |
| | | | | 180 | | | | | 185 | | | | | 190 | |

```
His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Ile His Tyr Asn Tyr Met Cys Asn Ser
225                     230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                     310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg
        355                 360
```

( 2 ) INFORMATION FOR SEQ ID NO:19:

( i ) SEQUENCE CHARACTERISTICS:
        ( A ) LENGTH: 363 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:19:

```
Met Glu Glu Pro Gln Ser Asp Pro Ser Val Glu Pro Pro Leu Ser Gln
1                   5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
        130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
```

|     |     |     |     |     | 180 |     |     |     | 185 |     |     |     | 190 |     |
| --- | --- | --- | --- | --- | --- | --- | --- | --- | --- | --- | --- | --- | --- | --- |
| His | Leu | Ile | Arg | Val | Glu | Gly | Asn | Leu | Arg | Val | Glu | Tyr | Leu | Asp | Asp |
|     |     | 195 |     |     |     |     | 200 |     |     |     |     | 205 |     |     |     |
| Arg | Asn | Thr | Phe | Arg | His | Ser | Val | Val | Pro | Tyr | Glu | Pro | Pro | Glu |
|     |     | 210 |     |     |     |     | 215 |     |     |     |     | 220 |     |     |
| Val | Gly | Ser | Asp | Cys | Thr | Thr | Ile | His | Tyr | Asn | Tyr | Met | Cys | Asn | Ser |
| 225 |     |     |     |     | 230 |     |     |     |     | 235 |     |     |     |     | 240 |
| Ser | Cys | Met | Gly | Gly | Met | Asn | Gln | Arg | Pro | Ile | Leu | Thr | Ile | Ile | Thr |
|     |     |     |     | 245 |     |     |     |     | 250 |     |     |     |     | 255 |     |
| Leu | Glu | Asp | Ser | Ser | Gly | Asn | Leu | Leu | Gly | Arg | Asn | Ser | Phe | Glu | Val |
|     |     |     | 260 |     |     |     |     | 265 |     |     |     |     | 270 |     |     |
| Arg | Val | Cys | Ala | Cys | Pro | Gly | Arg | Asp | Arg | Arg | Thr | Glu | Glu | Glu | Asn |
|     |     | 275 |     |     |     |     | 280 |     |     |     |     | 285 |     |     |     |
| Leu | Arg | Lys | Lys | Gly | Glu | Pro | His | His | Glu | Leu | Pro | Pro | Gly | Ser | Thr |
|     | 290 |     |     |     |     | 295 |     |     |     |     | 300 |     |     |     |     |
| Lys | Arg | Ala | Leu | Pro | Asn | Asn | Thr | Ser | Ser | Ser | Pro | Gln | Pro | Lys | Lys |
| 305 |     |     |     |     | 310 |     |     |     |     | 315 |     |     |     |     | 320 |
| Lys | Pro | Leu | Asp | Gly | Glu | Tyr | Phe | Thr | Leu | Gln | Ile | Arg | Gly | Arg | Glu |
|     |     |     |     | 325 |     |     |     |     | 330 |     |     |     |     | 335 |     |
| Arg | Phe | Glu | Met | Phe | Arg | Glu | Leu | Asn | Glu | Ala | Leu | Glu | Leu | Lys | Asp |
|     |     |     | 340 |     |     |     |     | 345 |     |     |     |     | 350 |     |     |
| Ala | Gln | Ala | Gly | Lys | Glu | Pro | Gly | Gly | Ser | Arg |     |     |     |     |     |
|     |     | 355 |     |     |     |     | 360 |     |     |     |     |     |     |     |     |

( 2 ) INFORMATION FOR SEQ ID NO:20:

( i ) SEQUENCE CHARACTERISTICS:
        ( A ) LENGTH: 363 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:20:

| Met | Glu | Glu | Pro | Gln | Ser | Asp | Pro | Ser | Val | Glu | Pro | Pro | Leu | Ser | Gln |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Glu | Thr | Phe | Ser | Asp | Leu | Trp | Lys | Leu | Leu | Pro | Glu | Asn | Asn | Val | Leu |
|     |     |     | 20 |     |     |     |     | 25 |     |     |     |     | 30 |     |     |
| Ser | Pro | Leu | Pro | Ser | Gln | Ala | Met | Asp | Asp | Leu | Met | Leu | Ser | Pro | Asp |
|     |     |     | 35 |     |     |     |     | 40 |     |     |     |     | 45 |     |     |
| Asp | Ile | Glu | Gln | Trp | Phe | Thr | Glu | Asp | Pro | Gly | Pro | Asp | Glu | Ala | Pro |
|     | 50 |     |     |     |     | 55 |     |     |     |     | 60 |     |     |     |     |
| Arg | Met | Pro | Glu | Ala | Ala | Pro | Pro | Val | Ala | Pro | Ala | Pro | Ala | Ala | Pro |
| 65 |     |     |     |     | 70 |     |     |     |     | 75 |     |     |     |     | 80 |
| Thr | Pro | Ala | Ala | Pro | Ala | Pro | Ala | Pro | Ser | Trp | Pro | Leu | Ser | Ser | Ser |
|     |     |     |     | 85 |     |     |     |     | 90 |     |     |     |     | 95 |     |
| Val | Pro | Ser | Gln | Lys | Thr | Tyr | Gln | Gly | Ser | Tyr | Gly | Phe | Arg | Leu | Gly |
|     |     |     |     | 100 |     |     |     |     | 105 |     |     |     |     | 110 |     |
| Phe | Leu | His | Ser | Gly | Thr | Ala | Lys | Ser | Val | Thr | Cys | Thr | Tyr | Ser | Pro |
|     |     |     | 115 |     |     |     |     | 120 |     |     |     |     | 125 |     |     |
| Ala | Leu | Asn | Lys | Met | Phe | Cys | Gln | Leu | Ala | Lys | Thr | Cys | Pro | Val | Gln |
|     |     |     | 130 |     |     |     |     | 135 |     |     |     |     | 140 |     |     |
| Leu | Trp | Val | Asp | Ser | Thr | Pro | Pro | Pro | Gly | Thr | Arg | Val | Arg | Ala | Met |
| 145 |     |     |     |     | 150 |     |     |     |     | 155 |     |     |     |     | 160 |
| Ala | Ile | Tyr | Lys | Gln | Ser | Gln | His | Met | Thr | Glu | Val | Val | Arg | Arg | Cys |
|     |     |     |     | 165 |     |     |     |     | 170 |     |     |     |     | 175 |     |

| | | | | | | | | | | | | | | |
|---|---|---|---|---|---|---|---|---|---|---|---|---|---|---|
|Pro|His|His|Glu|Arg|Cys|Ser|Asp|Ser|Asp|Gly|Leu|Ala|Pro|Pro|Gln|
| | |180| | | | |185| | | | |190| | |
|His|Leu|Ile|Arg|Val|Glu|Gly|Asn|Leu|Arg|Val|Glu|Tyr|Leu|Asp|Asp|
| | |195| | | |200| | | | |205| | | |
|Arg|Asn|Thr|Phe|Arg|His|Ser|Val|Val|Val|Pro|Tyr|Glu|Pro|Pro|Glu|
|210| | | | |215| | | | |220| | | | |
|Val|Gly|Ser|Asp|Cys|Thr|Thr|Ile|His|Tyr|Asn|Tyr|Met|Cys|Asn|Ser|
|225| | | | |230| | | |235| | | | |240|
|Ser|Cys|Met|Gly|Gly|Met|Asn|Gln|Arg|Pro|Ile|Leu|Thr|Ile|Ile|Thr|
| | | |245| | | | |250| | | | |255| |
|Leu|Glu|Asp|Ser|Ser|Gly|Asn|Leu|Leu|Gly|Arg|Asn|Ser|Phe|Glu|Val|
| | |260| | | |265| | | | |270| | | |
|Arg|Val|Cys|Ala|Cys|Pro|Gly|Arg|Asp|Arg|Arg|Arg|Glu|Glu|Glu|Asn|
| | |275| | | |280| | | | |285| | | |
|Leu|Arg|Lys|Lys|Gly|Glu|Pro|His|His|Glu|Leu|Pro|Pro|Gly|Ser|Thr|
| |290| | | | |295| | | | |300| | | |
|Lys|Arg|Ala|Leu|Pro|Asn|Asn|Thr|Ser|Ser|Ser|Pro|Gln|Pro|Lys|Lys|
|305| | | | |310| | | |315| | | | |320|
|Lys|Pro|Leu|Asp|Gly|Glu|Tyr|Phe|Thr|Leu|Gln|Ile|Arg|Gly|Arg|Glu|
| | | |325| | | | |330| | | | |335| |
|Arg|Phe|Glu|Met|Phe|Arg|Glu|Leu|Asn|Glu|Ala|Leu|Glu|Leu|Lys|Asp|
| | | |340| | | |345| | | | |350| | |
|Ala|Gln|Ala|Gly|Lys|Glu|Pro|Gly|Gly|Ser|Arg| | | | | |
| | |355| | | |360| | | | | | | | | |

( 2 ) INFORMATION FOR SEQ ID NO:21:

( i ) SEQUENCE CHARACTERISTICS:
( A ) LENGTH: 363 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO:21:

| | | | | | | | | | | | | | | |
|---|---|---|---|---|---|---|---|---|---|---|---|---|---|---|
|Met|Glu|Glu|Pro|Gln|Ser|Asp|Pro|Ser|Val|Glu|Pro|Pro|Leu|Ser|Gln|
|1| | | |5| | | | |10| | | | |15| |
|Glu|Thr|Phe|Ser|Asp|Leu|Trp|Lys|Leu|Leu|Pro|Glu|Asn|Asn|Val|Leu|
| | | |20| | | | |25| | | | |30| | |
|Ser|Pro|Leu|Pro|Ser|Gln|Ala|Met|Asp|Asp|Leu|Met|Leu|Ser|Pro|Asp|
| | |35| | | | |40| | | | |45| | | |
|Asp|Ile|Glu|Gln|Trp|Phe|Thr|Glu|Asp|Pro|Gly|Pro|Asp|Glu|Ala|Pro|
| |50| | | | |55| | | | |60| | | | |
|Arg|Met|Pro|Glu|Ala|Ala|Pro|Pro|Val|Ala|Pro|Ala|Pro|Ala|Ala|Pro|
|65| | | | |70| | | | |75| | | | |80|
|Thr|Pro|Ala|Ala|Pro|Ala|Pro|Ala|Pro|Ser|Trp|Pro|Leu|Ser|Ser|Ser|
| | | | |85| | | | |90| | | | |95| |
|Val|Pro|Ser|Gln|Lys|Thr|Tyr|Gln|Gly|Ser|Tyr|Gly|Phe|Arg|Leu|Gly|
| | | |100| | | | |105| | | | |110| | |
|Phe|Leu|His|Ser|Gly|Thr|Ala|Lys|Ser|Val|Thr|Cys|Thr|Tyr|Ser|Pro|
| | |115| | | | |120| | | | |125| | | |
|Ala|Leu|Asn|Lys|Met|Phe|Cys|Gln|Leu|Ala|Lys|Thr|Cys|Pro|Val|Gln|
| | |130| | | | |135| | | | |140| | | |
|Leu|Trp|Val|Asp|Ser|Thr|Pro|Pro|Pro|Gly|Thr|Arg|Val|Arg|Ala|Met|
|145| | | | |150| | | | |155| | | | |160|

```
Ala  Ile  Tyr  Lys  Gln  Ser  Gln  His  Met  Thr  Glu  Val  Val  Arg  Arg  Cys
               165                      170                         175

Pro  His  His  Glu  Arg  Cys  Ser  Asp  Ser  Asp  Gly  Leu  Ala  Pro  Pro  Gln
               180                      185                         190

His  Leu  Ile  Arg  Val  Glu  Gly  Asn  Leu  Arg  Val  Glu  Tyr  Leu  Asp  Asp
               195                      200                         205

Arg  Asn  Thr  Phe  Arg  His  Ser  Val  Val  Pro  Tyr  Glu  Pro  Pro  Glu
     210                          215                    220

Val  Gly  Ser  Asp  Cys  Thr  Thr  Ile  His  Tyr  Asn  Tyr  Met  Cys  Asn  Ser
225                      230                    235                         240

Ser  Cys  Met  Gly  Gly  Met  Asn  Arg  Arg  Pro  Ile  Leu  Thr  Ile  Ile  Thr
               245                      250                         255

Leu  Glu  Asp  Ser  Ser  Gly  Asn  Leu  Leu  Gly  Arg  Asn  Ser  Phe  Glu  Val
               260                      265                         270

His  Val  Cys  Ala  Cys  Pro  Gly  Arg  Asp  Arg  Arg  Thr  Glu  Glu  Glu  Asn
               275                      280                         285

Leu  Arg  Lys  Lys  Gly  Glu  Pro  His  His  Glu  Leu  Pro  Pro  Gly  Ser  Thr
     290                      295                         300

Lys  Arg  Ala  Leu  Pro  Asn  Asn  Thr  Ser  Ser  Ser  Pro  Gln  Pro  Lys  Lys
305                      310                         315                    320

Lys  Pro  Leu  Asp  Gly  Glu  Tyr  Phe  Thr  Leu  Gln  Ile  Arg  Gly  Arg  Glu
                    325                      330                         335

Arg  Phe  Glu  Met  Phe  Arg  Glu  Leu  Asn  Glu  Ala  Leu  Glu  Leu  Lys  Asp
               340                      345                         350

Ala  Gln  Ala  Gly  Lys  Glu  Pro  Gly  Gly  Ser  Arg
     355                      360
```

( 2 ) INFORMATION FOR SEQ ID NO:22:

( i ) SEQUENCE CHARACTERISTICS:
    ( A ) LENGTH: 363 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO:22:

```
Met  Glu  Glu  Pro  Gln  Ser  Asp  Pro  Ser  Val  Glu  Pro  Pro  Leu  Ser  Gln
1                   5                        10                         15

Glu  Thr  Phe  Ser  Asp  Leu  Trp  Lys  Leu  Leu  Pro  Glu  Asn  Asn  Val  Leu
               20                       25                         30

Ser  Pro  Leu  Pro  Ser  Gln  Ala  Met  Asp  Asp  Leu  Met  Leu  Ser  Pro  Asp
               35                       40                         45

Asp  Ile  Glu  Gln  Trp  Phe  Thr  Glu  Asp  Pro  Gly  Pro  Asp  Glu  Ala  Pro
     50                        55                       60

Arg  Met  Pro  Glu  Ala  Ala  Pro  Pro  Val  Ala  Pro  Ala  Pro  Ala  Ala  Pro
65                        70                       75                         80

Thr  Pro  Ala  Ala  Pro  Ala  Pro  Ala  Pro  Ser  Trp  Pro  Leu  Ser  Ser  Ser
                    85                       90                         95

Val  Pro  Ser  Gln  Lys  Thr  Tyr  Gln  Gly  Ser  Tyr  Gly  Phe  Arg  Leu  Gly
               100                      105                        110

Phe  Leu  His  Ser  Gly  Thr  Ala  Lys  Ser  Val  Thr  Cys  Thr  Tyr  Ser  Pro
          115                      120                        125

Ala  Leu  Asn  Lys  Met  Phe  Cys  Gln  Leu  Ala  Lys  Thr  Cys  Pro  Val  Gln
     130                      135                        140

Leu  Trp  Val  Asp  Ser  Thr  Pro  Pro  Pro  Gly  Thr  Arg  Val  Arg  Ala  Met
```

|       |       |       |       | 145   |       |       |       |       | 150   |       |       |       |       | 155   |       |       |       |       | 160   |
|-------|-------|-------|-------|-------|-------|-------|-------|-------|-------|-------|-------|-------|-------|-------|-------|-------|-------|-------|-------|
| Ala   | Ile   | Tyr   | Lys   | Gln   | Ser   | Gln   | His   | Met   | Thr   | Glu   | Val   | Val   | Arg   | Arg   | Cys   |
|       |       |       |       | 165   |       |       |       |       | 170   |       |       |       |       | 175   |       |
| Pro   | His   | His   | Glu   | Arg   | Cys   | Ser   | Asp   | Ser   | Asp   | Gly   | Leu   | Ala   | Pro   | Pro   | Gln   |
|       |       |       |       | 180   |       |       |       |       | 185   |       |       |       |       | 190   |       |
| His   | Leu   | Ile   | Arg   | Val   | Glu   | Gly   | Asn   | Leu   | Arg   | Val   | Glu   | Tyr   | Leu   | Asp   | Asp   |
|       |       |       |       | 195   |       |       |       |       | 200   |       |       |       |       | 205   |       |
| Arg   | Asn   | Thr   | Phe   | Arg   | His   | Ser   | Val   | Val   | Val   | Pro   | Tyr   | Glu   | Pro   | Pro   | Glu   |
|       |       |       |       | 210   |       |       |       |       | 215   |       |       |       |       | 220   |       |
| Val   | Gly   | Ser   | Asp   | Cys   | Thr   | Thr   | Ile   | His   | Tyr   | Asn   | Tyr   | Met   | Cys   | Asn   | Ser   |
| 225   |       |       |       |       |       |       |       |       | 230   |       |       |       |       | 235   |       |       |       |       | 240   |
| Ser   | Cys   | Met   | Gly   | Gly   | Met   | Asn   | Arg   | Arg   | Pro   | Ile   | Leu   | Thr   | Ile   | Ile   | Thr   |
|       |       |       |       | 245   |       |       |       |       | 250   |       |       |       |       | 255   |       |
| Leu   | Glu   | Asp   | Ser   | Ser   | Gly   | Asn   | Leu   | Leu   | Gly   | Arg   | Asn   | Ser   | Phe   | Glu   | Val   |
|       |       |       |       | 260   |       |       |       |       | 265   |       |       |       |       | 270   |       |
| His   | Val   | Cys   | Ala   | Cys   | Pro   | Gly   | Arg   | Asp   | Arg   | Arg   | Arg   | Thr   | Glu   | Glu   | Asn   |
|       |       |       |       | 275   |       |       |       |       | 280   |       |       |       |       | 285   |       |
| Leu   | Arg   | Lys   | Lys   | Gly   | Glu   | Pro   | His   | His   | Glu   | Leu   | Pro   | Pro   | Gly   | Ser   | Thr   |
|       |       |       |       | 290   |       |       |       |       | 295   |       |       |       |       | 300   |       |
| Lys   | Arg   | Ala   | Leu   | Pro   | Asn   | Asn   | Thr   | Ser   | Ser   | Ser   | Pro   | Gln   | Pro   | Lys   | Lys   |
| 305   |       |       |       |       |       |       |       |       | 310   |       |       |       |       | 315   |       |       |       |       | 320   |
| Lys   | Pro   | Leu   | Asp   | Gly   | Glu   | Tyr   | Phe   | Thr   | Leu   | Gln   | Ile   | Arg   | Gly   | Arg   | Glu   |
|       |       |       |       | 325   |       |       |       |       | 330   |       |       |       |       | 335   |       |
| Arg   | Phe   | Glu   | Met   | Phe   | Arg   | Glu   | Leu   | Asn   | Glu   | Ala   | Leu   | Glu   | Leu   | Lys   | Asp   |
|       |       |       |       | 340   |       |       |       |       | 345   |       |       |       |       | 350   |       |
| Ala   | Gln   | Ala   | Gly   | Lys   | Glu   | Pro   | Gly   | Gly   | Ser   | Arg   |
|       |       |       |       | 355   |       |       |       |       | 360   |       |

( 2 ) INFORMATION FOR SEQ ID NO:23:

( i ) SEQUENCE CHARACTERISTICS:
        ( A ) LENGTH: 363 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:23:

| Met   | Glu   | Glu   | Pro   | Gln   | Ser   | Asp   | Pro   | Ser   | Val   | Glu   | Pro   | Pro   | Leu   | Ser   | Gln   |
|-------|-------|-------|-------|-------|-------|-------|-------|-------|-------|-------|-------|-------|-------|-------|-------|
| 1     |       |       |       | 5     |       |       |       |       | 10    |       |       |       |       | 15    |       |
| Glu   | Thr   | Phe   | Ser   | Asp   | Leu   | Trp   | Lys   | Leu   | Leu   | Pro   | Glu   | Asn   | Asn   | Val   | Leu   |
|       |       |       |       | 20    |       |       |       |       | 25    |       |       |       |       | 30    |       |
| Ser   | Pro   | Leu   | Pro   | Ser   | Gln   | Ala   | Met   | Asp   | Asp   | Leu   | Met   | Leu   | Ser   | Pro   | Asp   |
|       |       |       |       | 35    |       |       |       |       | 40    |       |       |       |       | 45    |       |
| Asp   | Ile   | Glu   | Gln   | Trp   | Phe   | Thr   | Glu   | Asp   | Pro   | Gly   | Pro   | Asp   | Glu   | Ala   | Pro   |
|       |       |       |       | 50    |       |       |       |       | 55    |       |       |       |       | 60    |       |
| Arg   | Met   | Pro   | Glu   | Ala   | Ala   | Pro   | Pro   | Val   | Ala   | Pro   | Ala   | Pro   | Ala   | Ala   | Pro   |
| 65    |       |       |       |       |       |       |       |       | 70    |       |       |       |       | 75    |       |       |       |       | 80    |
| Thr   | Pro   | Ala   | Ala   | Pro   | Ala   | Pro   | Ala   | Pro   | Ser   | Trp   | Pro   | Leu   | Ser   | Ser   | Ser   |
|       |       |       |       | 85    |       |       |       |       | 90    |       |       |       |       | 95    |       |
| Val   | Pro   | Ser   | Gln   | Lys   | Thr   | Tyr   | Gln   | Gly   | Ser   | Tyr   | Gly   | Phe   | Arg   | Leu   | Gly   |
|       |       |       |       | 100   |       |       |       |       | 105   |       |       |       |       | 110   |       |
| Phe   | Leu   | His   | Ser   | Gly   | Thr   | Ala   | Lys   | Ser   | Val   | Thr   | Cys   | Thr   | Tyr   | Ser   | Pro   |
|       |       |       |       | 115   |       |       |       |       | 120   |       |       |       |       | 125   |       |
| Ala   | Leu   | Asn   | Lys   | Met   | Phe   | Cys   | Gln   | Leu   | Ala   | Lys   | Thr   | Cys   | Pro   | Val   | Gln   |
|       |       |       |       | 130   |       |       |       |       | 135   |       |       |       |       | 140   |       |

-continued

```
Leu  Trp  Val  Asp  Ser  Thr  Pro  Pro  Pro  Gly  Thr  Arg  Val  Arg  Ala  Met
145                      150                      155                      160

Ala  Ile  Tyr  Lys  Gln  Ser  Gln  His  Met  Thr  Glu  Val  Val  Arg  Arg  Cys
                    165                      170                      175

Pro  His  His  Glu  Arg  Cys  Ser  Asp  Ser  Asp  Gly  Leu  Ala  Pro  Pro  Gln
               180                      185                      190

His  Leu  Ile  Arg  Val  Glu  Gly  Asn  Leu  Arg  Val  Glu  Tyr  Leu  Asp  Asp
          195                      200                      205

Arg  Asn  Thr  Phe  Arg  His  Ser  Val  Val  Val  Pro  Tyr  Glu  Pro  Pro  Glu
     210                      215                      220

Val  Gly  Ser  Asp  Cys  Thr  Thr  Ile  His  Tyr  Asn  Tyr  Met  Cys  Asn  Ser
225                      230                      235                      240

Ser  Cys  Met  Gly  Gly  Met  Asn  Arg  Arg  Pro  Ile  Leu  Thr  Ile  Ile  Thr
                    245                      250                      255

Leu  Glu  Asp  Ser  Ser  Gly  Asn  Leu  Leu  Gly  Arg  Asn  Ser  Phe  Glu  Val
               260                      265                      270

Cys  Val  Cys  Ala  Cys  Pro  Gly  Arg  Asp  Arg  Arg  Thr  Glu  Glu  Glu  Asn
          275                      280                      285

Leu  Arg  Lys  Lys  Gly  Glu  Pro  His  His  Glu  Leu  Pro  Pro  Gly  Ser  Thr
     290                      295                      300

Lys  Arg  Ala  Leu  Pro  Asn  Asn  Thr  Ser  Ser  Ser  Pro  Gln  Pro  Lys  Lys
305                      310                      315                      320

Lys  Pro  Leu  Asp  Gly  Glu  Tyr  Phe  Thr  Leu  Gln  Ile  Arg  Gly  Arg  Glu
                    325                      330                      335

Arg  Phe  Glu  Met  Phe  Arg  Glu  Leu  Asn  Glu  Ala  Leu  Glu  Leu  Lys  Asp
               340                      345                      350

Ala  Gln  Ala  Gly  Lys  Glu  Pro  Gly  Gly  Ser  Arg
          355                      360
```

( 2 ) INFORMATION FOR SEQ ID NO:24:

( i ) SEQUENCE CHARACTERISTICS:
        ( A ) LENGTH: 363 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:24:

```
Met  Glu  Glu  Pro  Gln  Ser  Asp  Pro  Ser  Val  Glu  Pro  Pro  Leu  Ser  Gln
1                   5                        10                       15

Glu  Thr  Phe  Ser  Asp  Leu  Trp  Lys  Leu  Leu  Pro  Glu  Asn  Asn  Val  Leu
               20                       25                       30

Ser  Pro  Leu  Pro  Ser  Gln  Ala  Met  Asp  Asp  Leu  Met  Leu  Ser  Pro  Asp
          35                       40                       45

Asp  Ile  Glu  Gln  Trp  Phe  Thr  Glu  Asp  Pro  Gly  Pro  Asp  Glu  Ala  Pro
     50                       55                       60

Arg  Met  Pro  Glu  Ala  Ala  Pro  Pro  Val  Ala  Pro  Ala  Pro  Ala  Ala  Pro
65                       70                       75                       80

Thr  Pro  Ala  Ala  Pro  Ala  Pro  Ala  Pro  Ser  Trp  Pro  Leu  Ser  Ser  Ser
               85                       90                       95

Val  Pro  Ser  Gln  Lys  Thr  Tyr  Gln  Gly  Ser  Tyr  Gly  Phe  Arg  Leu  Gly
          100                      105                      110

Phe  Leu  His  Ser  Gly  Thr  Ala  Lys  Ser  Val  Thr  Cys  Thr  Tyr  Ser  Pro
     115                      120                      125
```

```
Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Cys Val Cys Ala Cys Pro Gly Arg Asp Arg Arg Glu Glu Asn
            275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg
            355                 360
```

( 2 ) INFORMATION FOR SEQ ID NO:25:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:25:

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
```

|     |     |     |     |     | 115 |     |     |     |     | 120 |     |     |     |     | 125 |     |     |
| --- | --- | --- | --- | --- | --- | --- | --- | --- | --- | --- | --- | --- | --- | --- | --- | --- | --- |
| Ala | Leu | Asn | Lys | Met | Phe | Cys | Gln | Leu | Ala | Lys | Thr | Cys | Pro | Val | Gln |     |     |
|     | 130 |     |     |     | 135 |     |     |     |     | 140 |     |     |     |     |     |     |     |
| Leu | Trp | Val | Asp | Ser | Thr | Pro | Pro | Gly | Thr | Arg | Val | Arg | Ala | Met |     |     |     |
| 145 |     |     |     |     | 150 |     |     |     |     | 155 |     |     |     |     | 160 |     |     |
| Ala | Ile | Tyr | Lys | Gln | Ser | Gln | His | Met | Thr | Glu | Val | Val | Arg | His | Cys |     |     |
|     |     |     |     | 165 |     |     |     |     | 170 |     |     |     |     |     | 175 |     |     |
| Pro | His | His | Glu | Arg | Cys | Ser | Asp | Ser | Asp | Gly | Leu | Ala | Pro | Pro | Gln |     |     |
|     |     |     | 180 |     |     |     |     | 185 |     |     |     |     | 190 |     |     |     |     |
| His | Leu | Ile | Arg | Val | Glu | Gly | Asn | Leu | Arg | Val | Glu | Tyr | Leu | Asp | Asp |     |     |
|     |     | 195 |     |     |     |     | 200 |     |     |     |     | 205 |     |     |     |     |     |
| Arg | Asn | Thr | Phe | Arg | His | Ser | Val | Val | Val | Pro | Tyr | Glu | Pro | Pro | Glu |     |     |
|     | 210 |     |     |     |     | 215 |     |     |     |     | 220 |     |     |     |     |     |     |
| Val | Gly | Ser | Asp | Cys | Thr | Thr | Ile | His | Tyr | Asn | Tyr | Met | Cys | Asn | Ser |     |     |
| 225 |     |     |     |     | 230 |     |     |     |     | 235 |     |     |     |     | 240 |     |     |
| Ser | Cys | Met | Gly | Gly | Met | Asn | Arg | Arg | Pro | Ile | Leu | Thr | Ile | Ile | Thr |     |     |
|     |     |     |     | 245 |     |     |     |     | 250 |     |     |     |     | 255 |     |     |     |
| Leu | Glu | Asp | Ser | Ser | Gly | Asn | Leu | Leu | Gly | Arg | Asn | Ser | Phe | Glu | Val |     |     |
|     |     |     | 260 |     |     |     |     | 265 |     |     |     |     | 270 |     |     |     |     |
| Arg | Val | Cys | Ala | Cys | Pro | Gly | Arg | Asp | Arg | Arg | Thr | Glu | Glu | Glu | Asn |     |     |
|     |     | 275 |     |     |     |     |     | 280 |     |     |     |     | 285 |     |     |     |     |
| Leu | Arg | Lys | Lys | Gly | Glu | Pro | His | His | Glu | Leu | Pro | Pro | Gly | Ser | Thr |     |     |
|     | 290 |     |     |     |     | 295 |     |     |     |     | 300 |     |     |     |     |     |     |
| Lys | Arg | Ala | Leu | Pro | Asn | Asn | Thr | Ser | Ser | Ser | Pro | Gln | Pro | Lys | Lys |     |     |
| 305 |     |     |     |     | 310 |     |     |     |     | 315 |     |     |     |     | 320 |     |     |
| Lys | Pro | Leu | Asp | Gly | Glu | Tyr | Phe | Thr | Leu | Gln | Ile | Arg | Gly | Arg | Glu |     |     |
|     |     |     |     | 325 |     |     |     |     | 330 |     |     |     |     | 335 |     |     |     |
| Arg | Phe | Glu | Met | Phe | Arg | Glu | Leu | Asn | Glu | Ala | Leu | Glu | Leu | Lys | Asp |     |     |
|     |     |     | 340 |     |     |     |     | 345 |     |     |     |     | 350 |     |     |     |     |
| Ala | Gln | Ala | Gly | Lys | Glu | Pro | Gly | Gly | Ser | Arg | Ala | His | Ser | Ser | His |     |     |
|     |     | 355 |     |     |     |     | 360 |     |     |     |     | 365 |     |     |     |     |     |
| Leu | Lys | Ser | Lys | Lys | Gly | Gln | Ser | Thr | Ser | Arg | His | Lys | Lys | Leu | Met |     |     |
|     | 370 |     |     |     |     | 375 |     |     |     |     | 380 |     |     |     |     |     |     |
| Phe | Lys | Thr | Glu | Gly | Pro | Asp | Ser | Asp |     |     |     |     |     |     |     |     |     |
| 385 |     |     |     |     | 390 |     |     |     |     |     |     |     |     |     |     |     |     |

( 2 ) INFORMATION FOR SEQ ID NO:26:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:26:

| Met | Glu | Glu | Pro | Gln | Ser | Asp | Pro | Ser | Val | Glu | Pro | Pro | Leu | Ser | Gln |
| --- | --- | --- | --- | --- | --- | --- | --- | --- | --- | --- | --- | --- | --- | --- | --- |
| 1 |     |     |     | 5 |     |     |     |     | 10 |     |     |     |     | 15 |     |
| Glu | Thr | Phe | Ser | Asp | Leu | Trp | Lys | Leu | Leu | Pro | Glu | Asn | Asn | Val | Leu |
|     |     |     | 20 |     |     |     |     | 25 |     |     |     |     | 30 |     |     |
| Ser | Pro | Leu | Pro | Ser | Gln | Ala | Met | Asp | Asp | Leu | Met | Leu | Ser | Pro | Asp |
|     |     | 35 |     |     |     |     | 40 |     |     |     |     | 45 |     |     |     |
| Asp | Ile | Glu | Gln | Trp | Phe | Thr | Glu | Asp | Pro | Gly | Pro | Asp | Glu | Ala | Pro |
|     | 50 |     |     |     |     | 55 |     |     |     |     | 60 |     |     |     |     |
| Arg | Met | Pro | Glu | Ala | Ala | Pro | Pro | Val | Ala | Pro | Ala | Pro | Ala | Ala | Pro |
| 65 |     |     |     |     | 70 |     |     |     |     | 75 |     |     |     |     | 80 |

```
Thr  Pro  Ala  Ala  Pro  Ala  Pro  Ala  Pro  Ser  Trp  Pro  Leu  Ser  Ser  Ser
               85              90                        95

Val  Pro  Ser  Gln  Lys  Thr  Tyr  Gln  Gly  Ser  Tyr  Gly  Phe  Arg  Leu  Gly
                100                 105                      110

Phe  Leu  His  Ser  Gly  Thr  Ala  Lys  Ser  Val  Thr  Cys  Thr  Tyr  Ser  Pro
          115                      120                125

Ala  Leu  Asn  Lys  Met  Phe  Cys  Gln  Leu  Ala  Lys  Thr  Cys  Pro  Val  Gln
     130                      135                      140

Leu  Trp  Val  Asp  Ser  Thr  Pro  Pro  Gly  Thr  Arg  Val  Arg  Ala  Met
145                      150                      155                      160

Ala  Ile  Tyr  Lys  Gln  Ser  Gln  His  Met  Thr  Glu  Val  Val  Arg  Arg  Cys
                165                      170                          175

Pro  His  His  Glu  Arg  Cys  Ser  Asp  Ser  Asp  Gly  Leu  Ala  Pro  Pro  Gln
               180                      185                          190

His  Leu  Ile  Arg  Val  Glu  Gly  Asn  Leu  Arg  Val  Glu  Tyr  Leu  Asp  Asp
          195                      200                 205

Arg  Asn  Thr  Phe  Arg  His  Ser  Val  Val  Val  Pro  Tyr  Glu  Pro  Pro  Glu
     210                      215                      220

Val  Gly  Ser  Asp  Cys  Thr  Thr  Ile  His  Tyr  Asn  Tyr  Met  Cys  Asn  Ser
225                      230                 235                          240

Ser  Cys  Met  Gly  Gly  Met  Asn  Trp  Arg  Pro  Ile  Leu  Thr  Ile  Ile  Thr
               245                      250                      255

Leu  Glu  Asp  Ser  Ser  Gly  Asn  Leu  Leu  Gly  Arg  Asn  Ser  Phe  Glu  Val
               260                      265                 270

Arg  Val  Cys  Ala  Cys  Pro  Gly  Arg  Asp  Arg  Arg  Thr  Glu  Glu  Glu  Asn
          275                      280                 285

Leu  Arg  Lys  Lys  Gly  Glu  Pro  His  His  Glu  Leu  Pro  Pro  Gly  Ser  Thr
     290                      295                      300

Lys  Arg  Ala  Leu  Pro  Asn  Asn  Thr  Ser  Ser  Ser  Pro  Gln  Pro  Lys  Lys
305                      310                      315                      320

Lys  Pro  Leu  Asp  Gly  Glu  Tyr  Phe  Thr  Leu  Gln  Ile  Arg  Gly  Arg  Glu
               325                      330                      335

Arg  Phe  Glu  Met  Phe  Arg  Glu  Leu  Asn  Glu  Ala  Leu  Glu  Leu  Lys  Asp
               340                      345                      350

Ala  Gln  Ala  Gly  Lys  Glu  Pro  Gly  Gly  Ser  Arg  Ala  His  Ser  Ser  His
          355                      360                      365

Leu  Lys  Ser  Lys  Lys  Gly  Gln  Ser  Thr  Ser  Arg  His  Lys  Lys  Leu  Met
     370                      375                      380

Phe  Lys  Thr  Glu  Gly  Pro  Asp  Ser  Asp
385                      390
```

( 2 ) INFORMATION FOR SEQ ID NO:27:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:27:

```
Met  Glu  Glu  Pro  Gln  Ser  Asp  Pro  Ser  Val  Glu  Pro  Pro  Leu  Ser  Gln
1               5                        10                            15

Glu  Thr  Phe  Ser  Asp  Leu  Trp  Lys  Leu  Leu  Pro  Glu  Asn  Asn  Val  Leu
               20                      25                       30
```

| | | | | | | | | | | | | | | |
|---|---|---|---|---|---|---|---|---|---|---|---|---|---|---|
|Ser|Pro|Leu 35|Pro|Ser|Gln|Ala|Met 40|Asp|Asp|Leu|Met 45|Leu|Ser|Pro|Asp|
|Asp|Ile 50|Glu|Gln|Trp|Phe|Thr 55|Glu|Asp|Pro|Gly|Pro 60|Asp|Glu|Ala|Pro|
|Arg 65|Met|Pro|Glu|Ala|Ala 70|Pro|Pro|Val|Ala|Pro 75|Ala|Pro|Ala|Ala|Pro 80|
|Thr|Pro|Ala|Ala|Pro 85|Ala|Pro|Ala|Pro|Ser 90|Trp|Pro|Leu|Ser|Ser 95|Ser|
|Val|Pro|Ser|Gln|Lys 100|Thr|Tyr|Gln|Gly|Ser 105|Tyr|Gly|Phe|Arg|Leu 110|Gly|
|Phe|Leu|His|Ser 115|Gly|Thr|Ala|Lys 120|Ser|Val|Thr|Cys 125|Thr|Tyr|Ser|Pro|
|Ala|Leu|Asn 130|Lys|Met|Phe|Cys 135|Gln|Leu|Ala|Lys|Thr 140|Cys|Pro|Val|Gln|
|Leu 145|Trp|Val|Asp|Ser|Thr 150|Pro|Pro|Gly|Thr|Arg 155|Val|Arg|Ala|Met 160| |
|Ala|Ile|Tyr|Lys|Gln 165|Ser|Gln|His|Met|Thr 170|Glu|Val|Val|Arg|Arg 175|Cys|
|Pro|His|His|Glu 180|Arg|Cys|Ser|Asp|Ser 185|Asp|Gly|Leu|Ala|Pro 190|Pro|Gln|
|His|Leu|Ile|Arg 195|Val|Glu|Gly|Asn|Leu 200|Arg|Val|Glu|Tyr|Leu 205|Asp|Asp|
|Arg|Asn|Thr 210|Phe|Arg|His|Ser 215|Val|Val|Val|Pro|Tyr 220|Glu|Pro|Pro|Glu|
|Val 225|Gly|Ser|Asp|Cys|Thr 230|Thr|Ile|His|Tyr|Asn 235|Tyr|Met|Cys|Asn|Ser 240|
|Ser|Cys|Met|Gly|Gly 245|Met|Asn|Arg|Ser|Pro 250|Ile|Leu|Thr|Ile|Ile 255|Thr|
|Leu|Glu|Asp|Ser 260|Ser|Gly|Asn|Leu|Leu 265|Gly|Arg|Asn|Ser|Phe 270|Glu|Val|
|Arg|Val|Cys 275|Ala|Cys|Pro|Gly|Arg 280|Asp|Arg|Arg|Thr|Glu 285|Glu|Glu|Asn|
|Leu|Arg 290|Lys|Lys|Gly|Glu|Pro 295|His|His|Glu|Leu|Pro 300|Pro|Gly|Ser|Thr|
|Lys 305|Arg|Ala|Leu|Pro|Asn 310|Asn|Thr|Ser|Ser|Ser 315|Pro|Gln|Pro|Lys|Lys 320|
|Lys|Pro|Leu|Asp|Gly 325|Glu|Tyr|Phe|Thr|Leu 330|Gln|Ile|Arg|Gly|Arg 335|Glu|
|Arg|Phe|Glu|Met 340|Phe|Arg|Glu|Leu|Asn 345|Glu|Ala|Leu|Glu|Leu 350|Lys|Asp|
|Ala|Gln|Ala|Gly 355|Lys|Glu|Pro|Gly|Gly 360|Ser|Arg|Ala|His|Ser 365|Ser|His|
|Leu|Lys|Ser 370|Lys|Lys|Gly|Gln|Ser 375|Thr|Ser|Arg|His|Lys 380|Lys|Leu|Met|
|Phe 385|Lys|Thr|Glu|Gly|Pro 390|Asp|Ser|Asp| | | | | | | |

( 2 ) INFORMATION FOR SEQ ID NO:28:

( i ) SEQUENCE CHARACTERISTICS:
        ( A ) LENGTH: 393 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:28:

| Met 1 | Glu | Glu | Pro | Gln 5 | Ser | Asp | Pro | Ser | Val 10 | Glu | Pro | Pro | Leu | Gln 15 |
|---|---|---|---|---|---|---|---|---|---|---|---|---|---|---|
| Glu | Thr | Phe | Ser 20 | Asp | Leu | Trp | Lys | Leu 25 | Leu | Pro | Glu | Asn | Asn 30 | Val | Leu |
| Ser | Pro | Leu 35 | Pro | Ser | Gln | Ala | Met 40 | Asp | Asp | Leu | Met | Leu 45 | Ser | Pro | Asp |
| Asp | Ile 50 | Glu | Gln | Trp | Phe | Thr 55 | Glu | Asp | Pro | Gly | Pro 60 | Asp | Glu | Ala | Pro |
| Arg 65 | Met | Pro | Glu | Ala | Ala 70 | Pro | Pro | Val | Ala | Pro 75 | Ala | Pro | Ala | Ala | Pro 80 |
| Thr | Pro | Ala | Ala | Pro 85 | Ala | Pro | Ala | Pro | Ser 90 | Trp | Pro | Leu | Ser | Ser 95 | Ser |
| Val | Pro | Ser | Gln | Lys 100 | Thr | Tyr | Gln | Gly | Ser 105 | Tyr | Gly | Phe | Arg | Leu 110 | Gly |
| Phe | Leu | His 115 | Ser | Gly | Thr | Ala | Lys 120 | Ser | Val | Thr | Cys | Thr 125 | Tyr | Ser | Pro |
| Ala | Leu | Asn 130 | Lys | Met | Phe | Cys | Gln 135 | Leu | Ala | Lys | Thr | Cys 140 | Pro | Val | Gln |
| Leu 145 | Trp | Val | Asp | Ser | Thr 150 | Pro | Pro | Pro | Gly | Thr 155 | Arg | Val | Arg | Ala | Met 160 |
| Ala | Ile | Tyr | Lys | Gln 165 | Ser | Gln | His | Met | Thr 170 | Glu | Val | Val | Arg | Arg 175 | Cys |
| Pro | His | His | Glu 180 | Arg | Cys | Ser | Asp | Ser 185 | Asp | Gly | Leu | Ala | Pro 190 | Pro | Gln |
| His | Leu | Ile 195 | Arg | Val | Glu | Gly | Asn 200 | Leu | Arg | Val | Glu | Tyr 205 | Leu | Asp | Asp |
| Arg | Asn 210 | Thr | Phe | Arg | His | Ser 215 | Val | Val | Val | Pro | Tyr 220 | Glu | Pro | Pro | Glu |
| Val 225 | Gly | Ser | Asp | Cys | Thr 230 | Thr | Ile | His | Tyr | Asn 235 | Tyr | Met | Cys | Asn | Ser 240 |
| Ser | Cys | Met | Gly | Gly 245 | Met | Asn | Arg | Arg | Pro 250 | Ile | Leu | Thr | Ile | Ile 255 | Thr |
| Leu | Glu | Asp | Ser 260 | Ser | Gly | Asn | Leu | Leu 265 | Gly | Arg | Asn | Ser | Phe 270 | Glu | Val |
| Arg | Val | Cys 275 | Ala | Cys | Pro | Gly | Arg 280 | Asp | Trp | Arg | Thr | Glu 285 | Glu | Glu | Asn |
| Leu | Arg 290 | Lys | Lys | Gly | Glu | Pro 295 | His | His | Glu | Leu | Pro 300 | Pro | Gly | Ser | Thr |
| Lys 305 | Arg | Ala | Leu | Pro | Asn 310 | Asn | Thr | Ser | Ser | Ser 315 | Pro | Gln | Pro | Lys | Lys 320 |
| Lys | Pro | Leu | Asp | Gly 325 | Glu | Tyr | Phe | Thr | Leu 330 | Gln | Ile | Arg | Gly | Arg 335 | Glu |
| Arg | Phe | Glu | Met 340 | Phe | Arg | Glu | Leu | Asn 345 | Glu | Ala | Leu | Glu | Leu 350 | Lys | Asp |
| Ala | Gln | Ala 355 | Gly | Lys | Glu | Pro | Gly 360 | Gly | Ser | Arg | Ala | His 365 | Ser | Ser | His |
| Leu | Lys 370 | Ser | Lys | Lys | Gly | Gln 375 | Ser | Thr | Ser | Arg | His 380 | Lys | Lys | Leu | Met |
| Phe 385 | Lys | Thr | Glu | Gly | Pro 390 | Asp | Ser | Asp |

( 2 ) INFORMATION FOR SEQ ID NO:29:

( i ) SEQUENCE CHARACTERISTICS:
   ( A ) LENGTH: 30 base pairs
   ( B ) TYPE: nucleic acid
   ( C ) STRANDEDNESS: double
   ( D ) TOPOLOGY: linear ( i i ) MOLECULE TYPE: other nucleic acid ( x i ) SEQUENCE DESCRIPTION: SEQ ID NO:29:

CCGGGCATGT CCGGGCATGT CCGGGCATGT                                                   30

( 2 ) INFORMATION FOR SEQ ID NO:30:

( i ) SEQUENCE CHARACTERISTICS:
      ( A ) LENGTH: 26 base pairs
      ( B ) TYPE: nucleic acid
      ( C ) STRANDEDNESS: double
      ( D ) TOPOLOGY: linear ( i i ) MOLECULE TYPE: other nucleic acid ( x i ) SEQUENCE DESCRIPTION: SEQ ID NO:30:

CCCGAACATG TCCCAACATG TTGGGG                                                       26

( 2 ) INFORMATION FOR SEQ ID NO:31:

( i ) SEQUENCE CHARACTERISTICS:
      ( A ) LENGTH: 27 base pairs
      ( B ) TYPE: nucleic acid
      ( C ) STRANDEDNESS: double
      ( D ) TOPOLOGY: linear ( i i ) MOLECULE TYPE: other nucleic acid ( x i ) SEQUENCE DESCRIPTION: SEQ ID NO:31:

ACAGAACATG TCTAAGCATG CTGGGGA                                                      27

( 2 ) INFORMATION FOR SEQ ID NO:32:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i ) MOLECULE TYPE: other nucleic acid ( x i ) SEQUENCE DESCRIPTION: SEQ ID NO:32:

ATCACGTGAT                                                                         10

( 2 ) INFORMATION FOR SEQ ID NO:33:

( i ) SEQUENCE CHARACTERISTICS:
      ( A ) LENGTH: 281 amino acids
      ( B ) TYPE: amino acid
      ( C ) STRANDEDNESS:
      ( D ) TOPOLOGY: linear ( i i ) MOLECULE TYPE: protein ( x i ) SEQUENCE DESCRIPTION: SEQ ID NO:33:

```
Met Ser Glu Tyr Gln Pro Ser Leu Phe Ala Leu Asn Pro Met Gly Phe
 1               5                  10                  15

Ser Pro Leu Asp Gly Ser Lys Ser Thr Asn Glu Asn Val Ser Ala Ser
             20                  25                  30

Thr Ser Thr Ala Lys Pro Met Val Gly Gln Leu Ile Phe Asp Lys Phe
         35                  40                  45

Ile Lys Thr Glu Glu Asp Pro Ile Ile Lys Gln Asp Thr Pro Ser Asn
```

-continued

```
                            50                                    55                                    60
      Leu  Asp  Phe  Asp  Phe  Ala  Leu  Pro  Gln  Thr  Ala  Thr  Ala  Pro  Asp  Ala
      65                  70                       75                            80

Lys  Thr  Val  Leu  Pro  Ile  Pro  Glu  Leu  Asp  Asp  Ala  Val  Val  Glu  Ser
                          85                       90                       95

Phe  Phe  Ser  Ser  Ser  Thr  Asp  Ser  Thr  Pro  Met  Phe  Glu  Tyr  Glu  Asn
                     100                      105                      110

Leu  Glu  Asp  Asn  Ser  Lys  Glu  Trp  Thr  Ser  Leu  Phe  Asp  Asn  Asp  Ile
                115                      120                           125

Pro  Val  Thr  Thr  Asp  Asp  Val  Ser  Leu  Ala  Asp  Lys  Ala  Ile  Glu  Ser
           130                 135                      140

Thr  Glu  Glu  Val  Ser  Leu  Val  Pro  Ser  Asn  Leu  Glu  Val  Ser  Thr  Thr
      145                      150                      155                           160

Ser  Phe  Leu  Pro  Thr  Pro  Val  Leu  Glu  Asp  Ala  Lys  Leu  Thr  Gln  Thr
                          165                      170                      175

Arg  Lys  Val  Lys  Lys  Pro  Asn  Ser  Val  Val  Lys  Lys  Ser  His  His  Val
                     180                      185                      190

Gly  Lys  Asp  Asp  Glu  Ser  Arg  Leu  Asp  His  Leu  Gly  Val  Val  Ala  Tyr
                195                           200                      205

Asn  Arg  Lys  Gln  Arg  Ser  Ile  Pro  Leu  Ser  Pro  Ile  Val  Pro  Glu  Ser
           210                      215                      220

Ser  Asp  Pro  Ala  Ala  Leu  Lys  Arg  Ala  Arg  Asn  Thr  Glu  Ala  Ala  Arg
      225                      230                      235                           240

Arg  Ser  Arg  Ala  Arg  Lys  Leu  Gln  Arg  Met  Lys  Gln  Ile  Glu  Asp  Lys
                          245                      250                           255

Leu  Glu  Glu  Ile  Leu  Ser  Lys  Leu  Tyr  His  Ile  Glu  Asn  Glu  Leu  Ala
                     260                      265                      270

Arg  Ile  Lys  Lys  Leu  Leu  Gly  Glu  Arg
                     275                      280
```

MODIFIED P53 CONSTRUCTS WHICH ENHANCE DNA BINDING

CROSS-REFERENCE TO RELATED APPLICATION

This is a continuation-in-part of U.S. Provisional patent application No. 60/004,802, filed Sep. 22, 1995.

FIELD OF THE INVENTION

The present invention relates generally to the field of oncoproteins, and more specifically to p53.

BACKGROUND OF THE INVENTION

Wild-type (wt) p53 is a sequence-specific DNA binding protein found in humans and other mammals, which has tumor suppressor function [See, e.g., Harris, *Science*, 262: 1980–1981 (1993)]. The wild-type p53 protein functions to regulate cell proliferation and cell death (also known as apoptosis). It also participates in the response of the cell to DNA damaging agents [Harris (1993), cited above]. In more than half of all human tumors p53 is inactivated by mutations and is therefore unable to arrest cell proliferation or induce apoptosis in response to DNA damaging agents, such as radiation and chemotherapeutics commonly used for cancer treatment. The nucleotide and amino acid sequences of human p53 have been reported by Zakut-Houri et al, *EMBO J.*, 4: 1251–1255 (1985); GenBank Code Hsp53]. The amino acid sequence of p53 is conserved across evolution [Soussi et al, *Oncogene*, 5: 945–952 (1990)], suggesting that its function is also conserved. The ability of p53 to bind DNA in a sequence-specific manner maps to amino acid residues 90–290 of human p53 [Halazonetis and Kandil, *EMBO J.*, 12: 5057–5064 (1993); Pavletich et al, *Genes Dev.*, 7: 2556–2564 (1993); Wang et al, *Genes Dev.*, 7: 2575–2586 (1993)] and the tetramerization domain maps to amino acid residues 322–355 of human p53.

Mutations of the p53 protein in most human tumors involve the sequence-specific DNA binding domain, so that the mutant proteins are unable to bind DNA [Bargonetti et al, *Genes Dev.*, 6: 1886–1898 (1992)]. The loss of p53 function is critical for tumor development. Of the two classes of tumor-derived p53 mutants, Class II mutants have unfolded DNA binding domains [Y. Cho et al, *Science*, 265:346–355 (1994); C. A. Finlay et al, *Mol. Cell. Biol.* 8:531–539 (1988)] and rescue of their DNA binding activity will require agents that stabilize their native structure, whereas Class I mutants retain a native-like three-dimensional structure, but have a substitution involving one of the residues that contact DNA [Y. Cho et al, cited above].

Introduction of wild-type p53 into tumor cells through gene therapy protocols has been proposed to be a viable approach to treat human cancer. See, e.g., T. Fujiwara et al, "Gene therapeutics and gene therapy for cancer", *Current Opinion in Oncoloqy*, 6:96–105 (1994); T. Friedmann, "Gene Therapy of Cancer through Restoration of Tumor-Suppressor Functions", *Cancer*, 70:1810–1817 (1992); International Patent Applications WO 9406910 A, WO 9416716 A, WO 9322430 A1, EP 390323, and EP 475623 A1.

There remains a need for a composition characterized by tumor suppressing activity and which is capable of replacing lost or insufficient p53 function.

SUMMARY OF THE INVENTION

The present invention provides a modified p53 protein construct having improved p53-DNA binding activity which is required for tumor suppressor activity, as compared to the unmodified p53 construct, and methods for obtaining such constructs. The method involves modifying a p53 construct containing a p53 DNA binding domain by substituting arginine at the amino acid corresponding to residue 284 of wild-type human p53.

In one aspect, the invention provides a modified p53 construct comprising a p53 amino acid sequence containing a DNA binding domain in which the threonine corresponding to amino acid residue 284 of the wild-type human p53 protein is changed to arginine.

In another aspect, the invention provides a method of enhancing the DNA-binding ability of a p53 construct having a p53 DNA binding domain comprising the step of modifying the codon encoding amino acid 284 to a codon encoding arginine.

In yet another aspect, the present invention provides a nucleic acid sequence encoding a protein of the invention. These nucleic acids may be inserted into an appropriate vector for delivery to patients for gene therapy. Alternatively the nucleic acids may be inserted into a vector for in vitro expression of a protein of the invention, which is then introduced into patients.

Other aspects and advantages of the present invention are described further in the following detailed description of the preferred embodiments thereof.

DETAILED DESCRIPTION OF THE INVENTION

Figure 1:
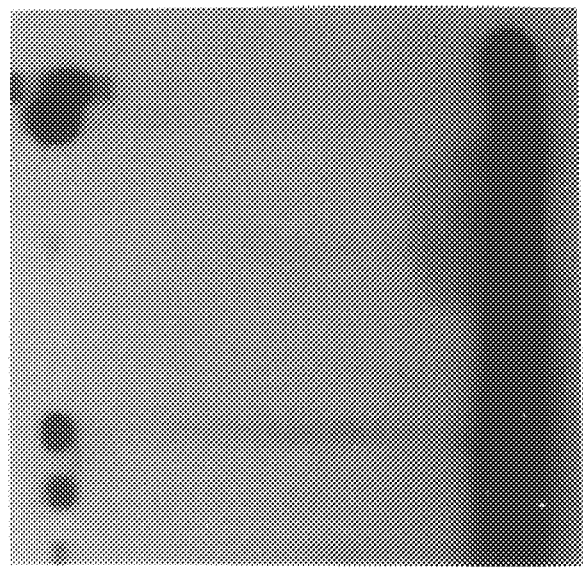
FIG. 1 illustrates activation of DNA binding of common Class I mutants by antibody PAb421. Binding was assayed using a high affinity DNA site (oligonucleotide BC) by gel retardation shift analysis on native electrophoretic gels. The amino acids are abbreviated using the single letter code: Cys, C; Gln, Q; His, H; Ser, S; Trp, W.

The present invention provides modified p53 constructs containing arginine at the amino acid residue corresponding to residue 284 of wild-type human p53 [SEQ ID NO: 2]. The inventor has found that such a modification results in an increase in the DNA binding avidity of the p53 and more efficient tumor suppression than the corresponding unmodified construct. For example, when wild-type p53 was so modified, the R284p53 [SEQ ID NO: 3] was found to bind DNA more avidly than wild-type p53 in vitro and to suppress colony growth of tumor cells about five- to six-fold more efficiently than wild-type p53 in tissue culture experiments. Particularly, the inventor demonstrates herein that the tumor suppressor function of common Class I tumor-derived p53 mutants can be restored and provides the means for pharmacological rescue of p53 function in cancer patients.

All references to human p53 residue numbers herein refer to the numbering scheme provided by Zakut-Houri et al, (1985) [cited above], which is incorporated by reference, and reproduced in SEQ ID NOS: 1 and 2.

Without wishing to be bound by theory, to fully restore DNA binding to tumor-derived p53 mutants, such as Gln248, His273 and cys273, the inventor introduced a novel p53-DNA contact between a phosphate of the DNA backbone and p53. This was done by replacing Thr284 of wild-type human p53 with Arg. This substitution, in conjunction with the conformational switch that involves the C-terminus of p53 and allosterically regulates the activity of the p53 DNA binding domain, fully restored DNA binding of the tumor-derived p53 mutants. Furthermore, the transcriptional and tumor suppressing activities of these p53 mutants were also restored. Thus, the inventor has demonstrated that the tumor suppressor function of common Class I tumor-derived p53 mutants can be restored and that p53 function can be rescued in cancer patients.

I. p53 Mutant Proteins

Thus, in one aspect the invention provides modified p53 protein constructs in which the amino acid residue corresponding to residue 284 of wild-type or native human p53 is modified from the native threonine to arginine. In an alternate, and currently less preferred, embodiment, the native Thr residue at position 284 may be substituted with Lys (K284). When Lys284 was introduced into a p53His273 mutant, it was found to bind oligonucleotide BC somewhat better than the original p53His273 mutant, using the assay described in detail in Example 3. It will be understood that where reference is made to R284 in the following discussion, K284 may be substituted.

The modified p53 constructs of the invention may be derived from full-length p53. p53Arg284 [SEQ ID NO:3] and p53Lys284 [SEQ ID NO:4] are examples of such modified constructs. Alternatively, the modified p53 constructs of the invention may contain a C-terminal p53 deletion. Currently a preferred deletion involves truncation of amino acid residues 364–393. One example of such a truncated construct is p53Arg284Δ364–393 [SEQ ID NO:17]. However, suitable deletions include truncation following amino acid residue 355, and deletions internal to this region (corresponding to residues 356–393 of SEQ ID NO:2).

As used herein, "p53 protein constructs" encompasses full-length and truncated p53 proteins containing a p53 DNA binding domain. Included in this definition are chimeric and mutant p53 proteins. Such proteins are known in the art.

Exemplary chimeric p53 proteins are described in detail in International Publication No. WO96/16989, published Jun. 6, 1996 and co-pending U.S. patent application Ser. No. 08/347,792 and co-pending U.S. patent application Ser. No. 08/431,357, which are incorporated by reference. For example, chimeric p53 proteins include proteins containing the N-terminal portion of p53 fused, optionally via a suitable linker, to a heterologous tetramerization domain. A heterologous tetramerization domain includes any sequence of amino acids heterologous to p53 which forms stable homotetramers. One particularly desirable tetramerization domain includes the tetrameric variant of the GCN4 LZ [Harbury et al, *Science*, 262:1401–1407 (1993)]. GCN4 numbering follows Hinnenbusch et al, *Proc. Natl. Acad. Sci. USA*, 81:6442–6446 (1984) and Ellenberger et al, *Cell*, 71:1223–1237 (1992). Wild-type GCN4 is provided in SEQ ID NOS: 5 and 6. The LZ variant has Ile at positions d of the coil and Leu at positions a [SEQ ID NO: 33], in contrast to the original zipper which has Leu and Val, respectively. Suitable chimera include (from N-terminus to C-terminus):

(a) aa 1–334 of p53wt [SEQ ID NO: 2], fused via an Asn linker, to a heterologous sequence spanning residues 249–281 of GCN4 containing isoleucines at positions d of the coiled coil and leucines at positions a [SEQ ID NO: 33];

(b) aa 1–334 of p53wt [SEQ ID NO: 2], fused via a Gly-Asn-Pro-Glu linker [SEQ ID NO: 7], to a heterologous sequence spanning residues 250–281 of GCN4 containing isoleucines at positions d of the coiled coil and leucines at positions a [SEQ ID NO: 33];

(c) aa 1–325 of p53wt [SEQ ID NO: 2], fused via an Arg-Gly-Asn linker [SEQ ID NO: 8], to the heterologous sequence of (a) above;

(d) aa 1–325 of p53wt [SEQ ID NO: 2], fused via an Arg-Gly-Gly-Asn-Pro-Glu linker [SEQ ID NO: 9], to the heterologous sequence of (b) above;

(e) aa 1–323 of p53wt [SEQ ID NO: 2], fused via an Arg-Gly-Asn linker [SEQ ID NO: 8], to the heterologous sequence of (a) above;

(f) aa 1–323 of p53wt [SEQ ID NO: 2], fused via an Arg-Gly-Gly-Asn-Pro-Glu linker [SEQ ID NO: 9], to the heterologous sequence of (b) above;

(g) aa 1–300 of p53wt [SEQ ID NO: 2], fused via a Gly-Gly-Asn-Gln-Ala linker [SEQ ID NO: 10], to the heterologous sequence of (b) above;

(h) aa 1–325 of p53wt [SEQ ID NO: 2], fused via an Arg-Gly-Asn linker [SEQ ID NO: 8], to the heterologous sequence of (a) above, fused via an Ile linker, to aa 352–393 of p53wt [SEQ ID NO: 2];

(i) aa 1–325 of p53wt [SEQ ID NO: 2], fused via an Arg-Gly-Gly-Asn-Pro-Glu linker [SEQ ID NO: 9], to the heterologous sequence of (b) above, which is fused via an Ile linker, to aa 352–393 of p53wt [SEQ ID NO: 2];

(j) aa 1–323 of p53wt [SEQ ID NO: 2], fused via an Arg-Gly-Asn linker [SEQ ID NO: 8], to the heterologous sequence of (a) above, which is fused via an Ile linker to aa 352–393 of p53wt [SEQ ID NO: 2];

(k) aa 1–325 of p53wt [SEQ ID NO: 2], fused via an Arg-Gly-Gly-Asn-Pro-Glu linker [SEQ ID NO: 9], to the heterologous sequence of (b) above, which is fused via an Ile linker, to aa residues 352–393 of p53wt [SEQ ID NO: 2]; and (l) aa 1–334 of p53wt [SEQ ID NO: 2], fused via an Asn linker, to the heterologous sequence of (a) above, which is fused via an Ile linker, to aa residues 352–393 of p53wt [SEQ ID NO: 2].

Also encompassed within the definition of "p53 protein constructs" are both naturally occurring and engineered mutant proteins. Exemplary mutants include p53 having glutamine at residue 248 (p53Q248) [SEQ ID NO: 11], p53 having histidine at residue 273 (p53H273) [SEQ ID NO: 12], and p53 having cysteine at residue 273 (p53C273) [SEQ ID NO: 13]. Other p53 mutants which may be susceptible to this R284 mutation are known in the art.

Modifying the p53 protein construct according to the method of the invention, involves altering the residue corresponding to aa residue 284 of human p53wt or of a p53 mutant containing the native Thr284 to Arg. This modification can be achieved by mutating the 284 codon using conventional site-directed mutagenesis techniques [R. Higuchi et al, in M. A. Innis et al, (eds.), *PCR Protocols: A Guide to Methods and Applications*, Academic Press, San Diego, pp. 177–183 (1990)]. For example, preferably, the native codon 284 (ACA) is modified by site-directed mutagenesis to CGA or preferably CGT, which encodes Arg. However, one of skill in the art can readily make alternative modifications resulting in an Arg codon at position 284. Alternatively, conventional chemical synthesis techniques may be used to generate a p53 sequence containing this modification.

II. Nucleic Acid Sequences Encoding Modified p53 Proteins of the Invention

The present invention further provides nucleic acid sequences encoding the modified p53 protein constructs of this invention. In addition to the coding strand, the nucleic acid sequences of the invention include the complementary DNA sequence representing the non-coding strand, the messenger RNA sequence, the corresponding cDNA sequence and the RNA sequence complementary to the messenger RNA sequence. The above nucleotide sequences can be included within larger DNA or RNA fragments, or may be interrupted by introns.

In another embodiment the nucleic acids encoding the modified proteins of the invention are present in the context of vectors suitable for amplification in prokaryotic or eukaryotic cells or for expression in cell-free extracts or lysates or in prokaryotic or eukaryotic cells. Many such vectors are known and many of these are commercially available. For example, plasmids with bacterial or yeast replication origins allow amplification in bacteria or yeast, respectively. Such vectors allow the production of large quantities of nucleic acids encoding the proteins of the invention, which nucleic acids can be used for gene therapy or for expression of the modified p53 proteins of the invention. Similarly, expression vectors are known. For example, the vector pGEM4 (Promega, Madison, Wis.) is suitable for expression of the p53 proteins in cell-free lysates, while the vector pSV2 [Mulligan et al, *Proc. Natl. Acad. Sci. USA*, 78:2072–2076 (1981)] is suitable for expression in mammalian cells. Such vectors allow the production of the modified proteins of the invention in vitro for analysis of their functional properties or for delivery to patients. Alternatively, one of skill in the art may readily select or construct another suitable expression vector.

III. Gene Therapy

The nucleic acid sequences of the invention may be inserted into a vector capable of targeting and infecting a desired cell, either in vivo or ex vivo for gene therapy, and causing the encoded modified p53 protein construct of this invention to be expressed by that cell. Many such viral vectors are useful for this purpose, e.g., adenoviruses, retroviruses and adeno-associated viruses (AAV) [Schreiber et al, *Biotechniques*, 14: 818–823 (1993); Davidson et al, *Nature Genetics*, 3: 219–223 (1993); Roessler et al, *J. Clin. Invest.*, 92: 1085–1092 (1993); Smythe et al, *Ann. Thorac. Surg.*, 57: 1395–1401 (1994); Kaplitt et al, *Nature Genetics*, 8: 148–154 (1994)]. There has already been success using viral vectors driving expression of wild-type p53 [Fujiwara et al, *Cancer Res.*, 53: 4129–4133 (1993); Fujiwara et al, *Cancer Res.*, 54: 2287–2291 (1994); Friedmann, *Cancer*, 70(6 Suppl): 1810–1817 (1992); Fujiwara et al, *Curr. Opin. Oncol.*, 6: 96–105 (1994)].

For use in gene therapy, these viral vectors containing nucleic acid sequences encoding a modified p53 protein construct of the invention, are prepared by one of skill in the art with resort to conventional techniques (see references mentioned above). For example, a recombinant viral vector, e.g. an adenovirus, of the present invention comprises DNA of at least that portion of the viral genome which is capable of infecting the target cells operatively linked to the nucleic acid sequences of the invention. By "infection" is generally meant the process by which a virus transfers genetic material to its host or target cell. Preferably, the virus used in the construction of a vector of the invention is rendered replication-defective to remove the effects of viral replication on the target cells. In such cases, the replication-defective viral genome can be packaged by a helper virus in association with conventional techniques.

Briefly, the vector(s) containing the nucleic acids encoding a protein of the invention is suspended in a pharmaceutically acceptable carrier, such as saline, and administered parenterally (or by other suitable means) in sufficient amounts to infect the desired cells and provide sufficient levels of p53 activity to arrest abnormal cellular proliferation. Other pharmaceutically acceptable carriers are well known to those of skill in the art. A suitable amount of the vector containing the chimeric nucleic acid sequences is between about $10^6$ to $10^9$ infectious particles per mL carrier. The delivery of the vector may be repeated as needed to sustain satisfactory levels of p53 activity, as determined by monitoring clinical symptoms.

As desired, this therapy may be combined with other therapies for the disease or condition being treated. For example, therapy involving the administration of a vector capable of expressing a modified p53 protein construct of the invention is well suited for use in conjunction with conventional cancer therapies, including surgery, radiation and chemotherapy.

Alternatively, nucleic acid sequences driving expression of a p53 protein of the invention may also be introduced as "naked DNA" by "carriers" other than viral vectors, such as liposomes, nucleic acid-coated gold beads or can simply be suspended in saline or the like and injected in situ [Fujiwara et al (1994), cited above; Fynan et al, *Proc. Natl. Acad. Sci. USA*, 90: 11478–11482 (1993); Cohen, *Science*, 259: 1691–1692 (1993); Wolff et al, *Biotechniques*, 11: 474–485 (1991)]. A suitable amount of nucleic acid is between about 10 μg to about 1 mg per mL carrier. However, one of skill in the art may modify the therapeutic dose as desired.

IV. Pharmaceutical Compositions

The modified p53 protein constructs of this invention may also be formulated into pharmaceutical compositions and administered using a therapeutic regimen compatible with the particular formulation. Pharmaceutical compositions within the scope of the present invention include compositions containing a protein of the invention in an effective amount to have the desired physiological effect, e.g. to arrest the growth of cancer cells without causing unacceptable toxicity for the patient.

Suitable carriers for parenteral administration include aqueous solutions of the active compounds in water-soluble or water-dispersible form, e.g. saline. Alternatively, suspensions of the active compounds may be administered in suitable conventional lipophilic carriers or in liposomes.

The compositions may be supplemented by active pharmaceutical ingredients, where desired. Optional antibacterial, antiseptic, and antioxidant agents in the compositions can perform their ordinary functions. The pharmaceutical compositions of the invention may further contain any of a number of suitable viscosity enhancers, stabilizers, excipients and auxiliaries which facilitate processing of the active compounds into preparations that can be used pharmaceutically. Preferably, these preparations, as well as those preparations discussed below, are designed for parenteral administration. However, compositions designed for oral or rectal administration are also considered to fall within the scope of the present invention.

Those of skill in the pharmaceutical art should be able to derive suitable dosages and schedules of administration. As used herein, the terms "suitable amount" or "effective amount" means an amount which is effective to treat the conditions referred to below. A preferred dose of a pharmaceutical composition containing a protein of this invention is generally effective above about 0.1 mg modified p53 protein, and preferably from about 1 mg to about 100 mg. Dosage units of such pharmaceutical compositions containing the proteins of this invention preferably contain about 1 mg to 5 g of the protein. These doses may be administered with a frequency necessary to achieve and maintain satisfactory p53 DNA binding and tumor suppressor activity levels. Although a preferred range has been described above, alternative doses for treatment of each type of tumor or other condition may be determined by those of skill in the art.

V. Therapeutic Indications

The nucleic acids and proteins of the invention can be introduced into human patients for therapeutic benefits in conditions characterized by insufficient wild-type p53 activity. As stated above, the nucleic acids of the invention may be introduced into the patient in the form of a suitable viral vector (or by direct DNA delivery) to harness the patient's cellular machinery to express the proteins of the invention in vivo. Alternatively, the proteins of the invention may be introduced into the patient in appropriate pharmaceutical formulations as described above.

As one example, the pharmaceutical compositions of this invention, containing a protein of the invention or a nucleic acid or a viral vector which express a protein of the invention in vivo, may be employed to induce the cellular defense to DNA damaging agents. Examples of DNA damaging agents include sunlight, UV irradiation, as well as radiation and chemotherapeutics used for cancer treatment. By administering a suitable amount of a composition of this invention, patients may tolerate higher doses of such DNA damaging agents.

Another therapeutic use of the compositions of this invention is in inducing apoptosis of specific cells, such as proliferating lymphocytes. According to this method of use, a suitable amount of an appropriate pharmaceutical composition of this invention is administered to a subject to enhance the development of immune tolerance. This method may employ both in vivo and ex vivo modes of administration. Preferably, this therapy is useful as the sole treatment or as an accessory treatment to prevent transplant rejection, or to treat autoimmune diseases, e.g., systemic lupus erythrematosis, rheumatoid arthritis and the like.

The pharmaceutical compositions of this invention may also be employed to restore p53 function in tumor cells. Desirably, a suitable amount of the composition of this invention is administered systemically, or locally to the site of the tumor with or without concurrent administration of conventional cancer therapy (i.e. DNA damaging agents).

Additionally, the compositions of this invention may be administered in methods to suppress cell proliferation in diseases other than cancers, which are characterized by aberrant cell proliferation. Among such diseases are included psoriasis, atherosclerosis and arterial restenosis. This method is conducted by administering a suitable amount of the selected composition systemically or locally to the patient.

These examples illustrate the preferred method for preparing exemplary modified p53 constructs of the invention and the biological activity of the modified p53 constructs. These examples are illustrative only and do not limit the scope of the invention.

EXAMPLE 1 p53 Protein Production

Plasmids of the PGEM series were used to generate in vitro translated p53 proteins, as previously described [T. Halazonetis and A. Kandil, *EMBO J.*, 12:5057–5064 (1993a); T. Halazonetis and A. Kandil, *EMBO J.*, 12:1021–1028 (1993b); J. L. Waterman et al, EMBO J., 14:512–519 (1995)].

More specifically, plasmid pGEMhump53wt (also termed pGEMhp53wtB) encodes full-length human wild-type p53. This plasmid was prepared by PCR using a human p53 cDNA, which is readily available to those practicing the art. The PCR procedure was designed to incorporate unique restriction sites within the coding sequence of human p53: Kpn I at codon 218, Sst I at codon 299, Sst II at codon 333, Bst BI at codon 338 and Sal I immediately following the termination codon. An Msc I site at codon 138 was eliminated. These changes did not alter the sequence of the encoded p53, and were only performed to expedite construction of mutant proteins bearing altered tetramerization domains or point mutations associated with human cancer. The PCR product of the human p53 cDNA was digested with Nco I and Sal I and cloned in the vector pGEM4 [Promega, Madison, Wis.], which was linearized with Eco RI and Sal I. Synthetic oligonucleotides were used to bridge the Eco RI site of the vector and the Nco I site at the initiation codon of p53. Plasmid, pGEMhump53wt, was used to generate all the p53 mutants and modified p53 protein constructs described below, as well as for expression of wild-type p53 by in vitro translation [J. L. F. Waterman et al, *EMBO J.*, 14:512–519 (1995)]. The proteins were derived from pGEMhump53wt by site-directed mutagenesis [Higuchi, in Innis et al, *PCR Protocols: A Guide to Methods and Application*, Academic Press, San Diego, pp. 177–183 (1990)] of the codons indicated below. In vitro translated proteins were expressed using SP6 transcribed mRNA and rabbit reticulocyte lysates, as previously described [Halazonetis et al, *Cell*, 55:917–925 (1988)].

The following proteins were generated in this manner:
a) Wild-type p53 (p53wt) [SEQ ID NO: 2]
b) Wild-type p53 containing the Thr284 to Arg substitution (p53R284) [SEQ ID NO: 3]

c) Tumor-derived mutant p53 glutamine 248 (p53Q248) [SEQ ID NO: 11]

d) Tumor-derived mutant p53 glutamine 248 containing the Thr284 to Arg substitution (p53Q248R284) [SEQ ID NO: 14]

e) Tumor-derived mutant p53 mutant histidine 273 (p53H273) [SEQ ID NO: 12]

f) Tumor-derived mutant p53 histidine 273 containing the Thr 284 to Arg substitution (p53H273R284) [SEQ ID NO: 15]

g) Tumor-derived mutant p53 cysteine 273 (p53C273) [SEQ ID NO: 13]

h) Tumor-derived mutant p53 cysteine 273 containing the Thr 284 to Arg substitution (p53C273R284) [SEQ ID NO: 16].

Proteins corresponding to a) to h), each containing a deletion of the C-terminal 30 amino acid of human p53 (Δ364-393), were also generated [SEQ ID NOS: 17–24]. These deletions permit in vitro DNA binding.

In addition, plasmid pSV2hp53wtB was used to express wild-type p53 in mammalian cells [M. J. F. Waterman et al, *Cancer Res.*, 56:158–163 (1996)]. Plasmid pBC/TKseap has one copy of oligonucleotide BC [Halazonetis, *EMBO J.*, 12:1021–1028 (1993) cloned in the Eco RV site of pTKseap [Waterman, 1996] and expresses secreted alkaline phosphatase in a p53-responsive manner.

EXAMPLE 2

DNA Binding Activity

The DNA binding activity of wild-type p53 is allosterically regulated by a basic region within the C-terminal 30 amino acids of p53. Monoclonal antibodies that mask this regulatory region, such as PAb421, or deletion of this region stimulate binding to DNA [T. Halanonetis et al, *EMBJO J.*, 12:1021–1028 (1993); T. R. Hupp et al, *Cell*, 71:875–886 (1992); J. L. F. Waterman et al, *EMBO J.*, 14:512–519 (1995)]. Interestingly, some tumor-derived mutants have also been reported to bind DNA when allosterically activated by antibody PAb421 [T. Halazonetis and A. Kandil, *EMBO J.*, 12:5057–5064 (1993); T. Hupp et al, *Nucl. Acids. Res.*, 21:3167–3174 (1993); D. Niewolik et al, *Oncogene*, 10:881–890 (1995)].

Figure 2:
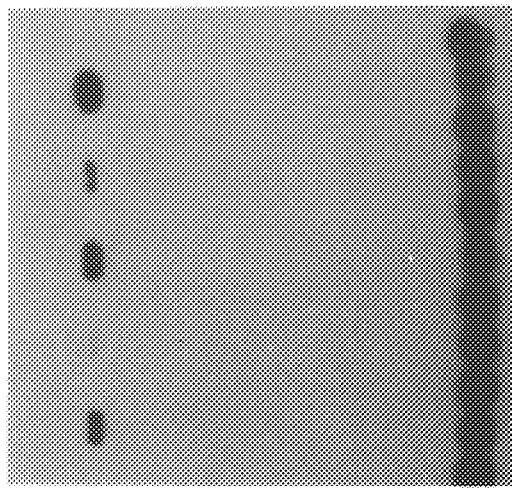
FIG. 2 illustrates activation of DNA binding of common Class I mutants by deletion of the p53 C-terminal 30 amino acids (residues 364–393). Binding was assayed using a high affinity DNA site (oligonucleotide BC) by gel retardation shift analysis on native electrophoretic gels in the presence of specific (S-oligonucleotide BC) or non-specific (NS-oligonucleotide TF3) unlabeled excess competitor DNA. The amino acids are abbreviated using the single letter code: Cys, C; Gln, Q; His, H; Ser, S; Trp, W.

The seven most common tumor-derived mutants: p53His175 [SEQ ID NO: 25], Gln248 [SEQ ID NO: 11], Trp248 [SEQ ID NO: 26], Ser249 [SEQ ID NO: 27], His273 [SEQ ID NO: 12], Trp282 [SEQ ID NO: 28] and Cys273 [SEQ ID NO: 13] [M. Hollstein et al, *Science*, 253:49–53 (1991)] were examined. The substitutions in these mutants target arginines 248 or 273 that contact DNA (Class I mutants) or arginines 175, 249 or 282 that stabilize the structure of the DNA binding domain (Class II mutants) [Y. Cho et al, *Science*, 265:346–355 (1994)]. Of the seven tumor-derived mutants, four recognized a high affinity p53 DNA site in the presence of PAb421 (FIG. 1) or when their C-terminal 30 amino acids were deleted (FIG. 2). Significantly, the mutants bound DNA in the presence of excess unlabeled non-specific DNA suggesting that they retain sequence specificity. Except for p53Trp248, allosteric activation enhanced DNA binding of all Class I mutants examined. DNA binding of Class II mutants was not activated, except for p53Trp282, which, like wild-type p53, bound DNA in the absence and presence of PAb421. Thus, Class I mutants, which retain a native structure of their DNA binding domain, have latent sequence-specific DNA binding activity, whereas Class II mutants, which have unfolded DNA binding domains [C. A. Finlay et al, *Mol. Cell. Biol.*, 8:531–539 (1988)], do not. Regarding the exceptions, we speculate that the large tryptophan side chain at position 248 precludes the p53Trp248 mutant from binding DNA due to steric interference with the DNA site. The ability of p53Trp282 to bind DNA may indicate that a small fraction of this mutant adopts the native fold.

Allosterically activated Class I p53 mutants compared favorably with wild-type p53 for binding to a high affinity DNA site. However, further experiments indicated that the mutants failed to recognize efficiently natural p53 sites, such as those present in the p21$^{cip1}$ and gadd45 genes [W. S. El-Deiry et al, *Cell*, 75:817–825 (1993), M. B. Kastan et al, *Cell*, 71:587–597 (1992)]. Since Class I p53 mutants apparently retain DNA binding sequence specificity, in an attempt to increase the affinity of Class I p53 mutants for DNA, novel protein-DNA backbone contacts were introduced. Towards this goal, residues of the DNA binding domain of p53His273 were replaced with basic amino acids. The substitutions targeted essentially all the residues close to the DNA backbone, except for those that already contact DNA or those that unequivocally stabilize the three-dimensional structure of p53 [Cho, cited above]. The targeted residues were: Gly117, Thr118, Ala119, Asn247, Thr284, Glu285 and Glu287.

Figure 3:
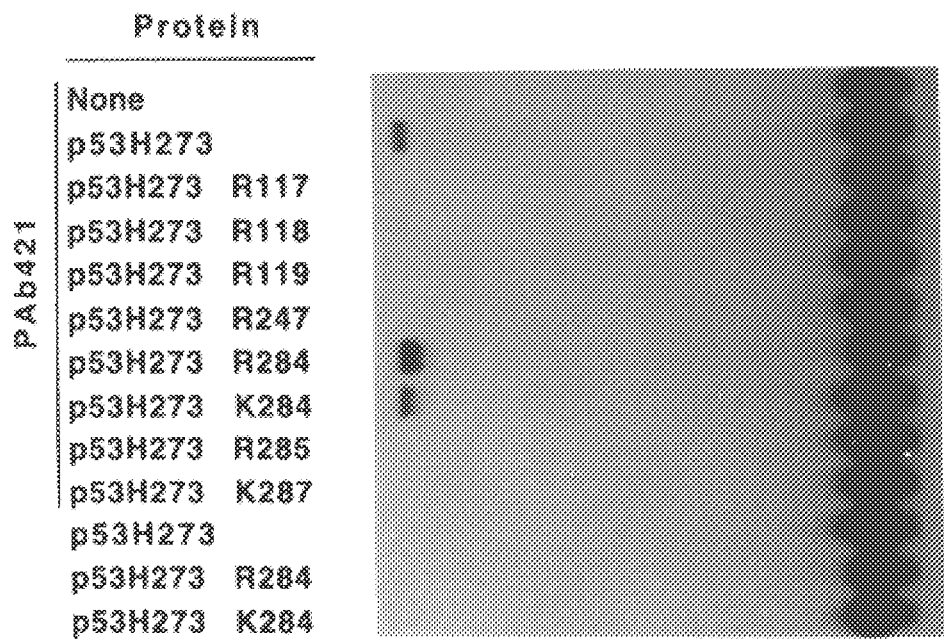
FIG. 3 illustrates the effects of a number of amino acid substitutions on DNA binding of the tumor-derived p53His273 mutant. Binding was assayed using a high affinity DNA site (oligonucleotide BC) by gel retardation shift analysis on native electrophoretic gels. The amino acids are abbreviated using the single letter code: His, H; Arg, R; Lys, K.

Substitution of Thr284 with Arg enhanced binding of p53His273 to the high affinity DNA site, although binding was still dependent on allosteric activation by antibody PAb421 (FIG. 3). Substitution of Thr284 with Lys also enhanced binding of p53His273 to the high affinity DNA site, but less than substitution of Thr284 with Arg. All other substitutions either suppressed or had no effect on p53His273 DNA binding (FIG. 3).

The effects of the substitution of Thr284 with Arg can be rationalized using molecular modeling. Specifically, using the coordinates of the wild-type p53 DNA binding domain bound to DNA [Cho, cited above] an Arg side chain introduced at position 284 could form electrostatic interactions with the phosphate oxygen atoms of DNA closest to its α-carbon and without violating bond lengths and angles. Modeling was performed with Quanta 4.1 (Molecular Simulations Inc., Burlington, Mass.).

In the following experiments, the effect of the Thr284 to Arg substitution on binding to natural DNA sites was examined in the context of wild-type p53, of p53His273 and of the other Class I p53 mutants.

All the proteins of Example 1 containing the 30 amino acid C-terminal deletion were expressed by in vitro translation and assayed for DNA binding using 0.2 ng $^{32}$P-labeled DNA and, where indicated below, 100 ng unlabeled competitor DNA [J. L. F. Waterman et al, *EMBO J.*, 14512–519 (1995)], The analysis was restricted to the C-terminally truncated proteins because full-length p53 translated in vitro is in a latent state and cannot bind DNA unless activated by a C-terminal truncation or by a monoclonal antibody (PAb421) that binds to the p53 C-terminus [Waterman et al, cited above].

For analysis of DNA binding activity, these proteins were incubated with $^{32}$P-labeled oligonucleotides and subjected to electrophoresis as described [Halazonetis (1993a and 1993b) and Waterman (1995), both cited above]. Oligonucleotide BC, which has the following sequence (top strand) is: [SEQ ID NO: 29] CC-GGGCA-TGTCC-GGGCA-TGTCC-GGGCATGT, and oligonucleotide Ep21, which has the following sequence: [SEQ ID NO: 30] CCC-GAACA-TGTCC-CAACA-TGTTG-GGG, each contain a p53 binding site, which is underlined. The BC oligonucleotide has a high affinity p53-binding site, while oligonucleotide Ep21contains a lower affinity site, which is present in the regulatory sequences of the p21 gene [W. S. El-Deiry et al, *Cell*, 75:817–825 (1993)]. Oligonucleotide Egadd45has the sequence [SEQ ID NO: 31] ACA-GAACA-TGTCT-AAGCA-TGCTG-GGGA. Oligonucleotide TF3, which contains three tandem repeats of [SEQ ID NO: 32] ATCACGTGAT, is a non-specific DNA [Halazonetis et al, *EMBO J.*, 12:1021–1028 (1993)].

Figure 4:
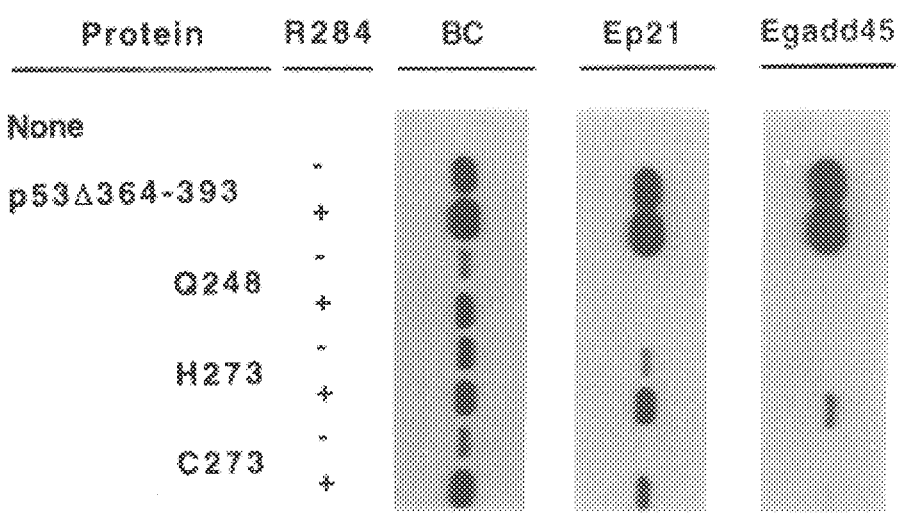
FIG. 4 illustrates the effect of the Thr284 to Arg substitution on binding of wild-type p53 and tumor-derived p53 mutants to a high affinity DNA site, and to the sites in the $p21^{cip1}$ and gadd45 genes (oligonucleotides BC, Ep21 and Egadd45, respectively). Binding was assayed by gel retardation shift analysis on native electrophoretic gels. Only the region of the gel corresponding to the p53-DNA complexes is shown. The amino acids are abbreviated using the single letter code: Arg, R; Cys, C; Gln, Q; His, H; Lys, K.

The Thr284 to Arg substitution enhanced binding of all p53 proteins examined (FIG. 4). For wild-type p53 the effect is evident with oligonucleotides BC and Ep21, for p53Gln248 it is evident with oligonucleotide BC, for p53His273 and p53Cys273 it is evident with all oligonucleotides tested (FIG. 4).

EXAMPLE 3

Transcription and Tumor Suppression Assays

The proteins of Example 1 were examined for their transcriptional activity and tumor suppressor activity. Wild-type p53 activates transcription of target genes and suppresses tumor growth, whereas tumor-derived mutants lack both these activities [S. E. Kern et al, *Science*, 256:827–830 (1992); C. A. Finlay et al, *Cell*, 57:1083–1093 (1989)]. The transcriptional activities of wild-type p53 and various p53 mutants were assayed with a p53-responsive reporter plasmid in Saos-2 human osteosarcoma cells, which lack endogenous p53 [M. J. F. Waterman et al, *Cancer Res.*, 56:158–163 (1996)].

More particularly, transcriptional activity was determined by transfecting Saos-2 cells with 2.5 μg pSV2hp53 expression plasmid and 27.5 μg pBC/TKseap or pTKseap reporter plasmids [Waterman et al, *Cancer Res.*, 56:158–163 (1996)]. The Class I p53 mutants had either weak (p53His273) or no (p53Gln248 and p53Cys273) transcriptional activity. However, their transcriptional activity was enhanced to wild-type levels by the Thr284 to Arg substitution or, for p53Gln248, by combining the Thr284 to Arg substitution with C-terminal allosteric activation (FIG. 1).

Tumor suppressing activity was tested in a colony formation assay, by cotransfecting Saos-2 osteosarcoma cells with 5 μg of pSV2hp53 expression plasmid directing p53 expression, 0.5 μg of pSV7neo, a plasmid that confers neomycin/G418 resistance [K. Zhang et al, *Proc. Natl. Acad. Sci. USA*, 87:6281–6285 (1990)] and 24 μg of pBC12/PLseap [T. D. Halazonetis, *Anticancer Res.*, 12:285–292 (1992)], a carrier plasmid. The transfected cells were selected for G418 resistance, a neomycin relative. Two weeks later the colonies were stained with crystal violet and counted. High tumor suppressor activity corresponds to low colony formation.

TABLE 1

| Expressed Protein | SEQ ID NO: | Tumor Colonies (mean ± 1 S.E.) |
|---|---|---|
| Human wild-type p53 | 2 | 11.3 ± 3.3 |
| Human p53Δ364–393 | 17 | 17.7 ± 4.8 |
| Human p53Arg284 | 3 | 2.0 ± 1.0 |
| Human p53Arg284Δ364–393 | 18 | 4.7 ± 0.7 |

Figure 5:
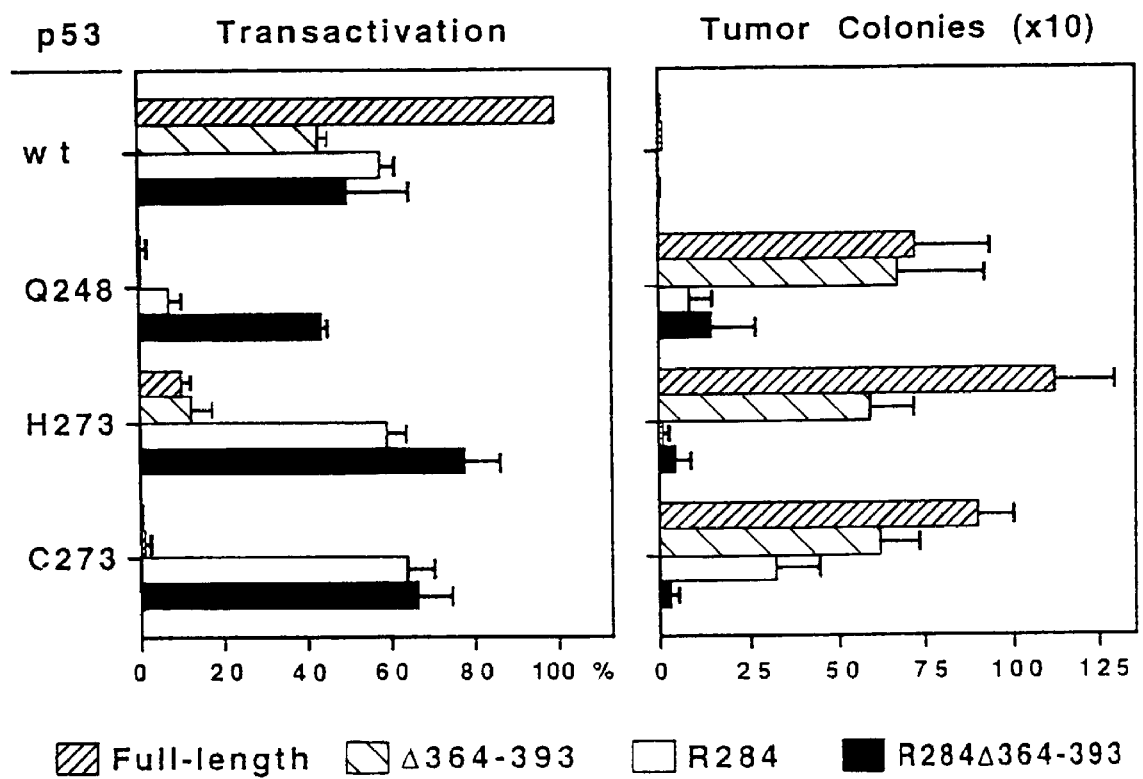
FIG. 5 illustrates the results of an experiment relating to rescue of the transcriptional and tumor suppressor activities of tumor-derived p53 mutants. Transcriptional activities from a reporter plasmid containing a high affinity p53 DNA site (oligonucleotide BC) are presented as means ±SE. The activity of wild-type p53 was adjusted to 100%. No transcription was detected from a reporter lacking a p53 site. Tumor suppressor activities in Saos-2 osteosarcoma cells are presented as means ±SE of the number of tumor cell colonies per plate. The amino acids are abbreviated using the single letter code: Arg, R; Cys, C; Gln, Q; His, H.

As illustrated in Table 1 above and in FIG. 5, the proteins containing the Arg284 modification suppressed tumor colony formation more efficiently than the corresponding proteins without the Arg284 modification (Table 1). The magnitude of the effect is greater for the tumor-derived p53 mutants; however, even the tumor suppressor activity of wild-type p53 is enhanced by the Arg284 modification.

While the effect of the Arg284 modification seems to be greater for tumor-derived mutants, rather than wild-type p53, this is a reflection of the limitations of the assays used. In these assays, wild-type p53 demonstrates high activity. If the assays were adjusted so that wild-type p53 would have low activity, then the effect of the Arg284 modification would be as dramatic as observed with the tumor-derived p53 mutants.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A modified p53 protein construct having DNA binding ability comprising a p53 sequence selected from the group consisting of:
   (a) a sequence that differs from at least about amino acid 90 to about amino acid 290 of the sequence of SEQ ID NO:2 by the substitution of threonine at position 284 by arginine; and
   (b) a sequence that differs from at least about amino acid 90 to about amino acid 290 of the sequence of SEQ ID NO:2 by the substitution of threonine at position 284 by arginine and by the substitution addition, or deletion of up to 20 amino acids.

2. The modified p53 protein construct according to claim 1 wherein the p53 sequence is full-length human wild-type human p53.

3. The modified p53 protein construct according to claim 1 wherein the p53 sequence is human wild-type p53 bearing a deletion of all or a fragment of the C-terminal residues 356 to 393.

4. The modified p53 protein construct according to claim 1 wherein the p53 sequence is a tumor-derived or engineered mutant p53.

5. The modified p53 protein construct according to claim 4 wherein the p53 sequence is a tumor-derived p53 mutant having an amino acid sequence selected from the group consisting of: a mutant p53 having glutamine at amino acid position 248, a mutant p53 having histidine at amino acid position 273, and a mutant p53 having cysteine at amino acid position 273.

6. The modified p53 protein construct according to claim 1 wherein the p53 sequence is deleted of all or a fragment of the C-terminal residues 356 to 393.

7. The modified p53 protein construct according to claim 1 wherein the p53 sequence is a chimeric p53 protein.

8. The modified p53 protein construct according to claim 4 wherein the p53 sequence contains an engineered p53 DNA binding domain.

9. A method of enhancing the DNA-binding ability of a p53 protein construct comprising the steps of:
   (a) providing a nucleic acid sequence encoding a p53 protein construct comprising a p53 sequence selected from the group consisting of:
      (i) at least about amino acid 90 to about amino acid 290 of the sequence of SEQ ID NO:2; and
      (ii) a sequence which differs from at least about amino acid 90 to about amino acid 290 of the sequence of SEQ ID NO:2 by the substitution, addition or deletion of up to 20 amino acids; and
   (b) modifying the codon encoding threonine residue 284 to a codon encoding arginine, whereby the resulting modified p53 protein construct is characterized by enhanced DNA-binding ability.

10. The method according to claim 9 wherein the p53 protein construct is amino acid sequence is a tumor-derived or engineered mutant p53.

11. The method according to claim 9 wherein the p53 protein construct is a chimeric p53 protein.

12. A nucleotide sequence encoding a modified p53 protein construct according to claim 1.

13. A vector comprising a nucleotide sequence encoding a modified p53 protein construct according to claim 1.

14. A modified p53 protein construct having DNA binding ability comprising a p53 sequence selected from the group consisting of:
 (a) a sequence that differs from at least about amino acid 90 to about amino acid 290 of the sequence of SEQ ID NO:2 by the substitution of threonine at position 284 of by lysine; and
 (b) a sequence that differs from at least about amino acid 90 to about amino acid 290 of the sequence of SEO ID NO:2 by the substitution of threonine at position 284 by lysine and by the substitution addition, or deletion of up to 20 amino acids.

15. A method of enhancing the DNA-binding ability of a p53 protein construct, comprising the steps of:
 (a) providing a nucleic acid sequence encoding a p53 protein construct comprising a p53 sequence selected from the group consisting of:
  (i) at least about amino acid 90 to about amino acid 290 of the sequence of SEQ ID:2; and
  (ii) a sequence which differs from at least about amino acid 90 to about amino acid 290 of the sequence of SEQ ID NO:2 by the substitution, addition or deletion of up to 20 amino acids; and
 (b) modifying the codon encoding threonine residue 284 to a codon encoding lysine, whereby the resulting modified p53 construct is characterized by enhanced DNA-binding ability.

16. A nucleotide sequence encoding a modified p53 protein construct according to claim 14.

17. A vector comprising a nucleotide sequence encoding a modified p53 protein construct according to claim 14.

18. A modified p53 protein construct having DNA binding ability comprising full-length human wild-type p53 protein, SEQ ID NO:2, wherein the threonine at position 284 of the human p53 protein is changed to arginine.

* * * * *